(12) United States Patent
Hamel et al.

(10) Patent No.: US 7,256,695 B2
(45) Date of Patent: Aug. 14, 2007

(54) REMOTELY POWERED AND REMOTELY INTERROGATED WIRELESS DIGITAL SENSOR TELEMETRY SYSTEM

(75) Inventors: Michael John Hamel, Essex Junction, VT (US); Steven W. Arms, Williston, VT (US); Christopher P. Townsend, Shelburne, VT (US)

(73) Assignee: Microstrain, Inc., Williston, VT (US)

( * ) Notice: Subject to any disclaimer, the term of this patent is extended or adjusted under 35 U.S.C. 154(b) by 81 days.

(21) Appl. No.: 10/668,827

(22) Filed: Sep. 23, 2003

(65) Prior Publication Data

US 2004/0113790 A1    Jun. 17, 2004

Related U.S. Application Data

(60) Provisional application No. 60/412,725, filed on Sep. 23, 2002, provisional application No. 60/419,994, filed on Oct. 21, 2002.

(51) Int. Cl.
    *G08B 13/14*    (2006.01)
(52) U.S. Cl. ............................. 340/572.1; 340/572.4; 340/572.8; 340/870.16; 600/300; 600/492; 600/384
(58) Field of Classification Search ............. 340/572.1, 340/870.16, 870.1, 572.4, 572.8; 600/300, 600/492, 384; 235/492, 384; 325/384
    See application file for complete search history.

(56) References Cited

U.S. PATENT DOCUMENTS

| | | | | |
|---|---|---|---|---|
| 4,918,416 A | * | 4/1990 | Walton et al. | ............... 235/493 |
| 5,166,676 A | * | 11/1992 | Milheiser | .................. 340/10.34 |
| 5,446,447 A | * | 8/1995 | Carney et al. | ........... 340/572.4 |
| 5,597,534 A | * | 1/1997 | Kaiser | ...................... 422/82.02 |
| 5,680,106 A | * | 10/1997 | Schrott et al. | ........... 340/10.33 |
| 5,704,352 A | * | 1/1998 | Tremblay et al. | ............ 600/300 |
| 6,070,803 A | * | 6/2000 | Stobbe | ........................ 235/492 |
| 6,249,212 B1 | | 6/2001 | Beigel | |
| 2002/0024450 A1 | * | 2/2002 | Townsend et al. | ..... 340/870.16 |
| 2003/0225318 A1 | * | 12/2003 | Montegrande et al. | ....... 600/300 |

* cited by examiner

*Primary Examiner*—Tai Nguyen
(74) *Attorney, Agent, or Firm*—James Marc Leas

(57) ABSTRACT

An electronic system includes a reader and a remotely powered and remotely interrogated sensor transponder. The sensor transponder includes a coil or an antenna, a switched reactance circuit, a processor, and a sensor. The sensor transponder receives power radiated from the reader to the coil or antenna. The sensor uses the power for sensing. The sensor transponder is capable of processing sensor data in the processor and transmitting the sensor data to the reader using the switched reactance circuit. In one embodiment, the receiver coil or antenna is part of a resonant tank circuit which includes an impedance matching circuit. The impedance matching circuit is connected to the receiver coil or antenna to provide greater current to the sensor or other power-using device than would be available to the sensor or other power-using device if the sensor or other power-using device were connected between the first and second end. The impedance matching circuit can be two or more taps to the coil or antenna.

68 Claims, 29 Drawing Sheets

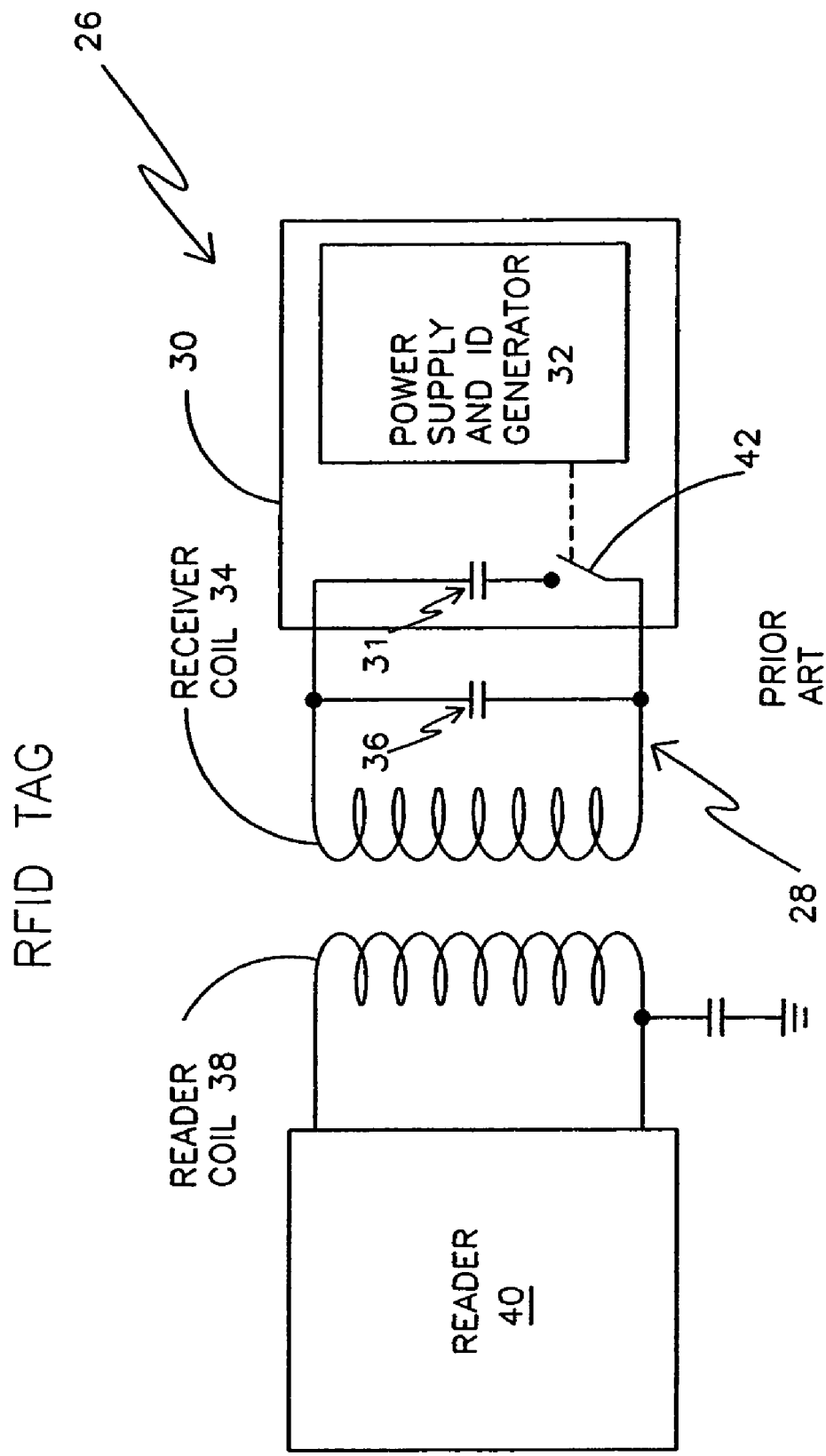

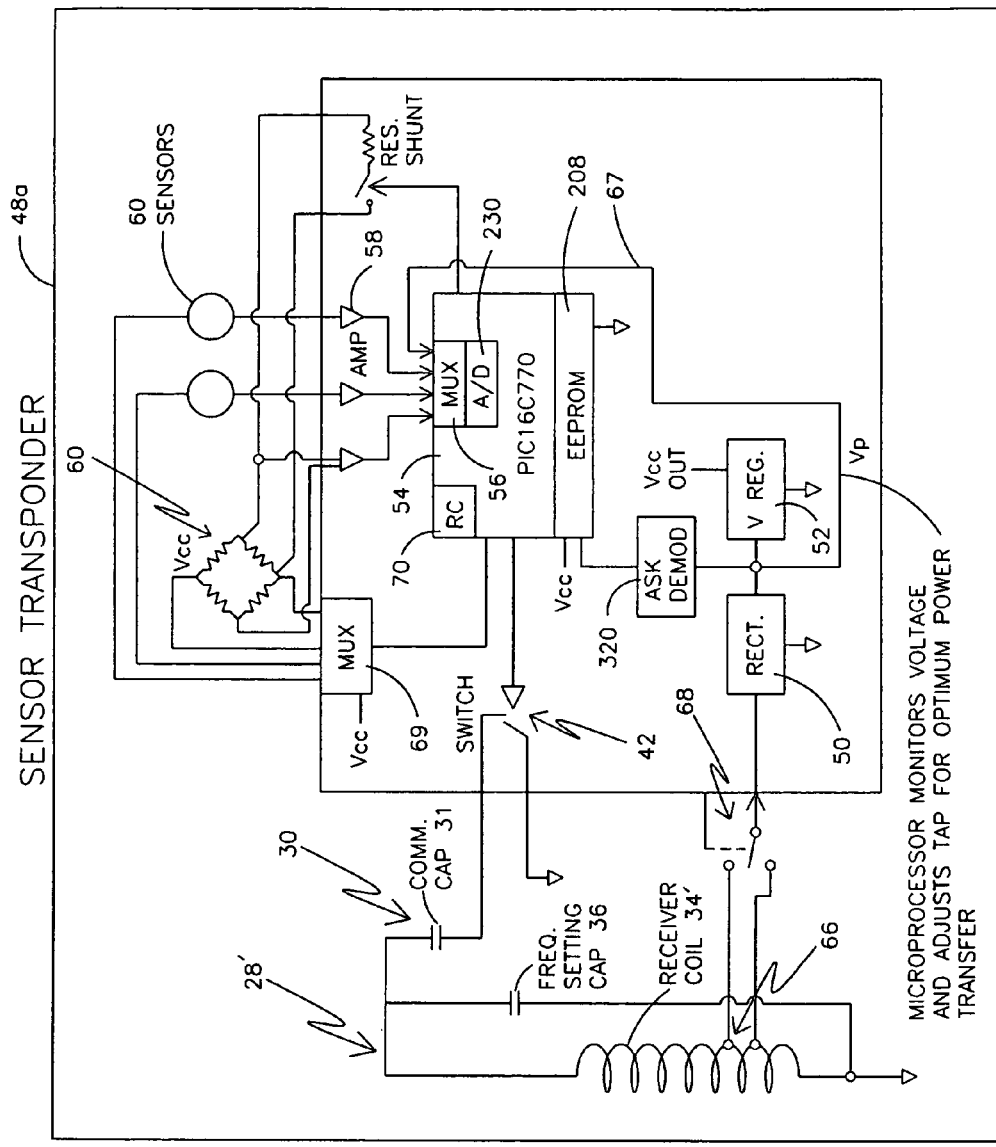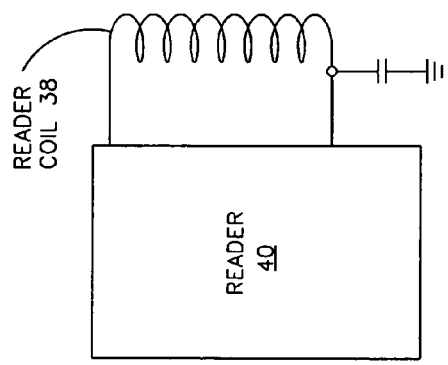
FIG. 2a

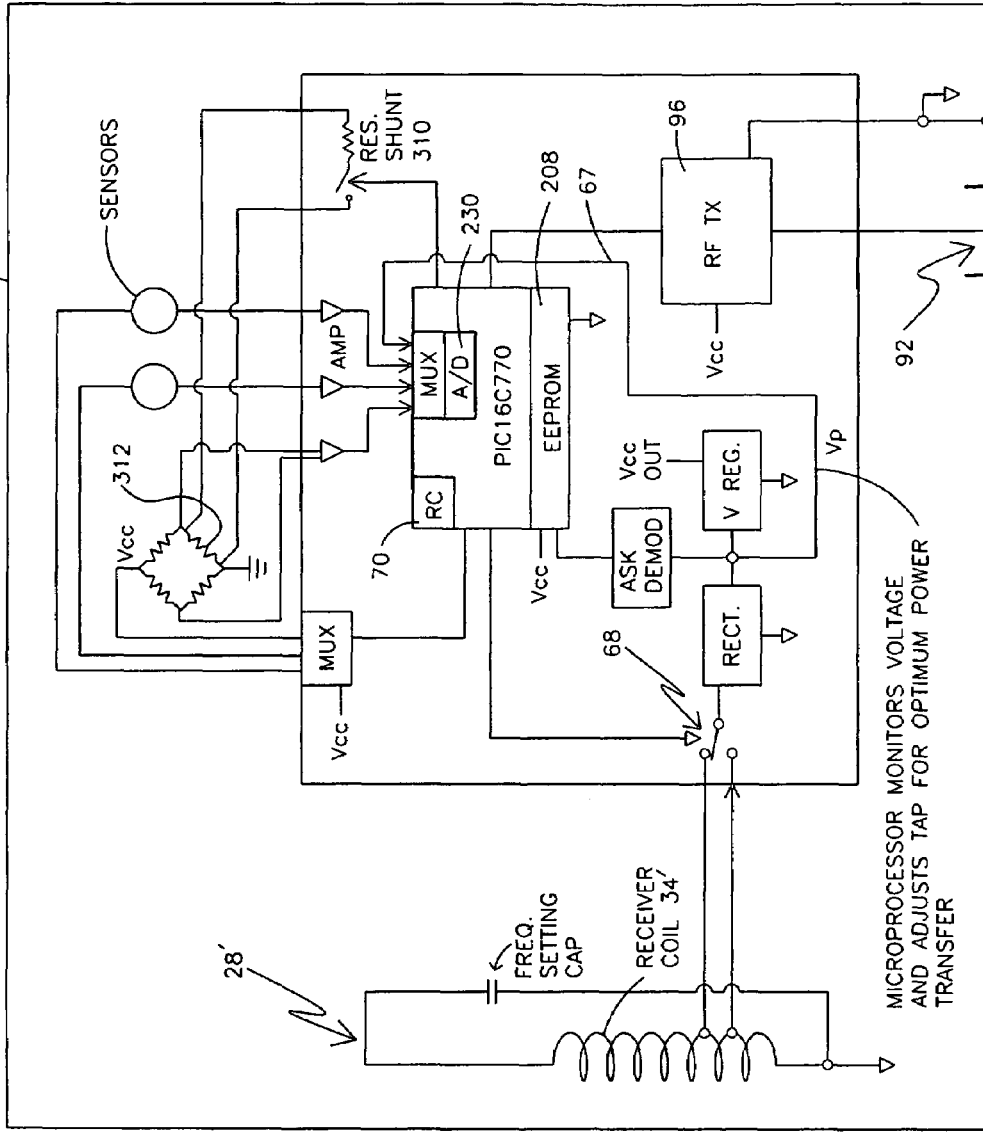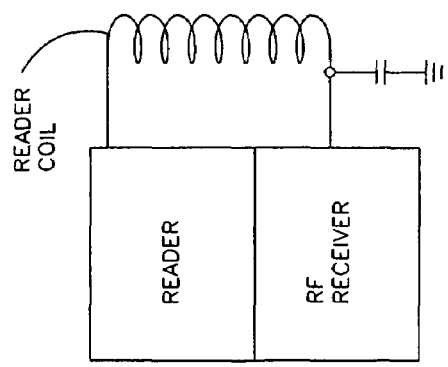
FIG. 2b

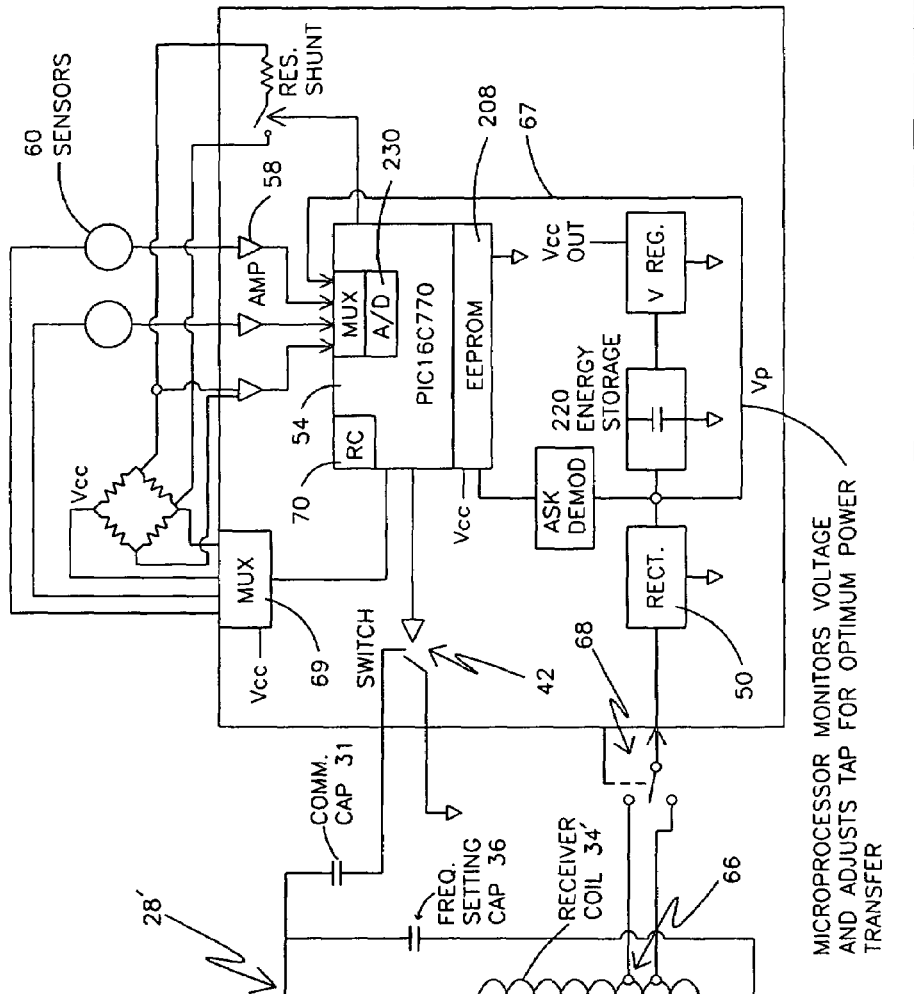
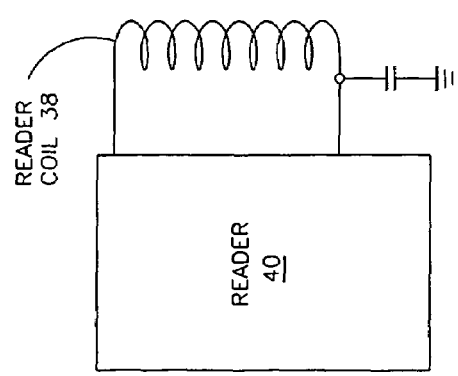
FIG. 2c

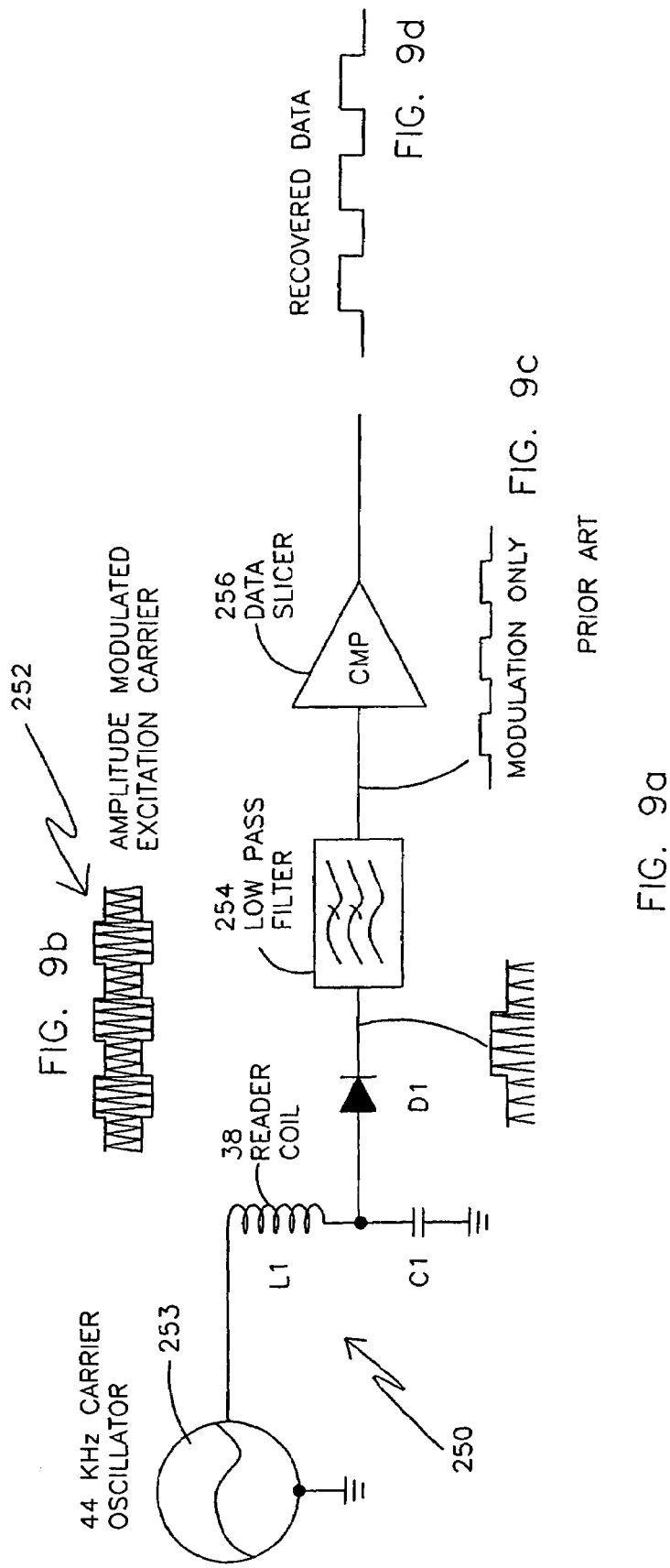

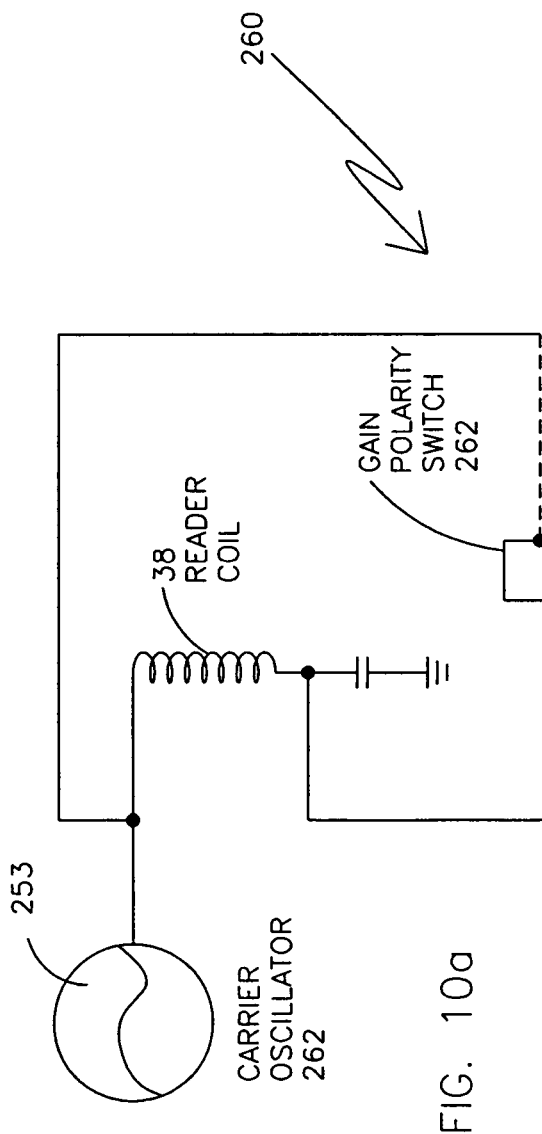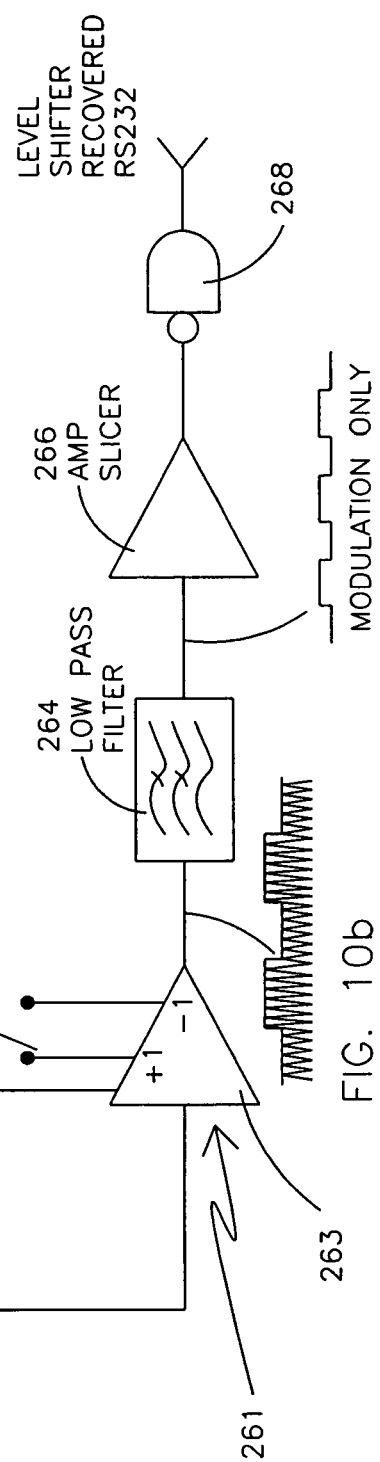

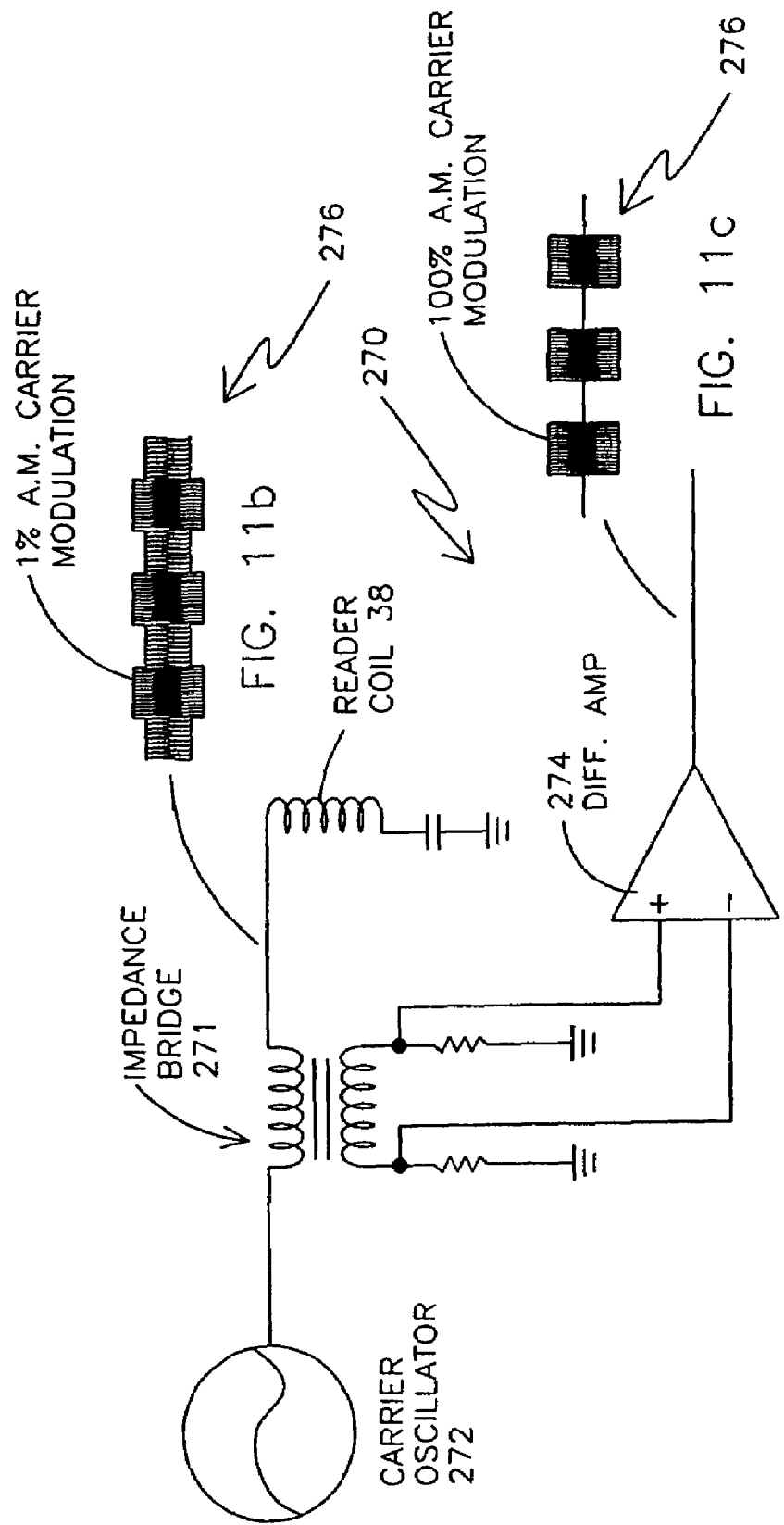

REMOTELY POWERED AND INTERROGATED CORROSION MEASURING DVRT SYSTEM W/SPRING ELEMENT

REMOTELY POWERED AND INTERROGATED CORROSION MEASURING DVRT SYSTEM W/O SPRING ELEMENT

REMOTELY POWERED AND INTERROGATED CORROSION MEASURING DVRT SYSTEM W/O SPRING ELEMENT

REMOTELY POWERED AND REMOTELY INTERROGATED WIRELESS DIGITAL SENSOR TELEMETRY SYSTEM

RELATED APPLICATIONS

This patent application is related to U.S. patent applications Ser. No. 09/731,066 09/801,230 and now U.S. Pat. No. 6,622,567, 09/768,858 and now U.S. Pat. No. 6,433,629, 10/215,752 which is a divisional of the U.S. Pat. No. 6,433,629, 09/114,106 and now U.S. Pat. No. 6,529,127, and U.S. patent application 10/379,224, which was a continuation of U.S. Provisional Patent Application 60/362,432, all of which are incorporated herein by reference.

This patent application claims priority of Provisional Patent Applications 60/412,725 filed on Sep. 23, 2002 and 60/419,994 filed on Oct. 21, 2002, both of which are entitled "Remotely Powered, Remotely Interrogated wireless Digital Sensor Telemetry System," and both of which are incorporated herein by reference. This application is a continuation-in-part of those Provisional Patent Applications.

FIELD OF THE INVENTION

This invention generally relates to sensors. More particularly, it relates to a circuit for wirelessly powering a sensor. Even more particularly, it relates to a circuit for remotely powering and interrogating a sensor.

BACKGROUND OF THE INVENTION

Sensors on civil structures, such as buildings, dams, and bridges and orthopedic implants, such as artificial hips and knees, have been limited because of the need to provide power for sensor operation and interrogation. In many of these applications retrieving sensor data precludes the use of batteries at the sensor or hardwired connections to the sensor. Very small spaces where common batteries will not fit, extremely harsh environments where common batteries would fail, and metallic hermetically sealed enclosures that would interfere with electromagnetic communication are among the many environments where sensor data retrieval is difficult.

Biomedical implants in which any sensor or electronic device must be hermetically sealed in a bio-compatible material such as titanium. It has been undesirable to use batteries for power because of the possibility of leakage. In addition, the implants must be as small as possible, limiting the size of batteries. Providing power to such sensors has been particularly difficult.

The rotating shaft of a turbine engine poses another type of challenge since centrifugal forces exceeding 80,000 G's with very high ambient temperatures is routine. Batteries cannot survive these forces and the high speed rotation precludes hardwiring or even slip-ring connections, which don't work reliably at such high RPM for extended periods of time. Furthermore, crystals commonly used for system timing, have not been able to withstand these forces making placement and reading of sensors in such locations difficult.

Thus, a better solution is needed to provide power and to read sensors that may be in inaccessible places or experiencing harsh environments where electric power is limited or where batteries cannot be easily recharged, and this solution is provided by the following invention.

SUMMARY OF THE INVENTION

It is therefore an object of the present invention to provide a scheme for powering and communicating with a sensor transponder that does not have an on-board source of power;

It is a further object of the present invention to provide for powering and communicating with a sensor transponder or other power using device using switched reactance;

It is a further object of the present invention to provide for powering and communicating with a device that is inside a hermetically sealed metal container without the need for an external antenna or feed through;

It is a feature of the present invention that a receiver coil is configured to impedance match with a power using load to improve efficiency;

It is a feature the present invention that power and communication can be provided to a device that is implanted in living tissue.

It is an advantage of the present invention that timing is provided without a crystal.

It is an advantage of the present invention that the sensor transponder can be configured to provide data storage.

It is an advantage of the present invention that the sensor transponder can be configured to power a device using more power than is available from the reader.

It is an advantage of the present invention that the sensor transponder can be configured to provide bi-directional communication.

BRIEF DESCRIPTION OF THE DRAWINGS

The foregoing and other objects, features, and advantages of the invention will be apparent from the following detailed description of the invention, as illustrated in the accompanying drawings, in which:

FIG. 1 is a schematic circuit diagram of a prior art RFID tag;

FIG. 2a is a circuit diagram of a reader and a sensor transponder of the present invention in which power is provided to a sensor through a tapped receiver coil or antenna and communication of sensor data is provided through a switched reactance connected to that receiver coil or antenna;

FIG. 2b is a circuit diagram of a reader and another embodiment of a sensor transponder of the present invention in which power is provided to a sensor through the tapped receiver coil or antenna and communication of sensor data is provided through an RF transmitter powered from the receiver coil or antenna;

FIG. 2c is a circuit diagram showing a circuit similar to that of FIG. 2a but also with on-board energy storage, such as a battery or storage capacitor;

FIG. 9a is a schematic block diagram of an embodiment of a reader having envelope demodulation of the carrier signal as modified by the switched reactance circuit of a sensor transponder of the present invention;

FIGS. 9b–9d are voltages at coil, after low pass filter, and after data slicer respectively in the process of envelope demodulation in the reader of FIG. 9a;

FIG. 10a is a schematic block diagram of another embodiment of a reader of the present invention providing synchronous AM demodulation of the carrier signal as modified by the switched reactance circuit of a sensor transponder of the present invention;

FIGS. 10b–10c are voltages at the output of an operational amplifier and after a low pass filter respectively in the process of synchronous demodulation in the reader of FIG. 10a;

FIG. 11a is a schematic block diagram of another embodiment of a reader of the present invention providing impedance bridge demodulation of the carrier signal as modified by the switched reactance circuit of a sensor transponder of the present invention;

FIGS. 11b–11c are voltages at the reader coil and after the differential amplifier respectively in the process of impedance bridge demodulation provided in the reader of FIG. 11a;

DETAILED DESCRIPTION OF THE PRESENT INVENTION

Figure 2D:
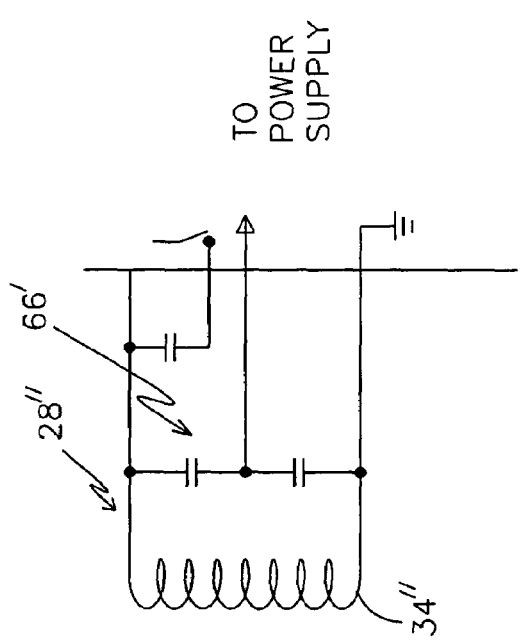
FIG. 2d is a circuit diagram showing a tank circuit that uses a capacitive divider instead of a tap for impedance matching.

The present invention substantially improves communication from switched reactance devices to enable powering a sensor transponder and communicate data from the sensor. Switched reactance circuits have advantage since they need no on-board power supply and receive all their power for operation from power transmitted to them by an external reader.

Remote electromagnetic powering with switched reactance communications has been used to power up and read identification codes on Radio Frequency IDentification (RFID) tags. RFID tag 26 has tank circuit 28 with its switched reactance circuit 30. Capacitor 31 of switched reactance circuit 30 is brought into or out of tank circuit 28 under the control of power supply and ID generator 32, as shown in FIG. 1. Switched reactance circuit 30 is powered through on board receiver coil 34 which, along with capacitor 36 makes up tank circuit 28. Receiver coil 34 can be a coil, as shown or it can be an antenna. In this application the phrase receiver coil will he used to cover both. Receiver coil 34 absorbs AC power from nearby radiating reader coil 38 connected to reader 40, as shown in FIGS. 1 and 2a. Reader coil 38 can also be either a coil or an antenna, and the phrase reader coil will be used to cover both. Power supply and ID generator 32 controls the position of switch 42 to determine whether communications capacitor 31 is connected or disconnected from tank circuit 28. Thus, reactance of tank circuit 28 is varied under the control of power supply and ID generator 32 so as to provide the RFID's digital code to reader 40.

Typically, RFID tags like RFID tag 26 shown in FIG. 1 are designed to respond to interrogation by providing only a specified digital ID code stored in non-volatile memory in the tag. Only a small amount of current and a small amount of energy are needed to power RFID tag 26 long enough to send this ID code, typically on the order of 6 uA and about 18 to 30 uJ, and this tiny amount of current and energy has been compatible with the amount of current and energy available through on-board receiver coil 34 from nearby radiating reader coil 38.

However, heretofore RFID tag technology has not been considered for reading sensors since several orders of magnitude more current and more energy are required to power and read most types of active sensors and to convert their information to digital format for the serial communications required in switched reactance sensor systems.

The present invention is not limited to power consuming sensors. It may also be used with other power using devices such as RF transmitters or actuators. The power consuming sensor can be a strain gauge, a displacement sensor, a corrosion sensor, a temperature or pressure sensor, or any other type of sensor. An actuator can include a solenoid, a pump, a motor, a mechanical switch, a piezoelectric device, or any other type of actuator.

The invention improves efficiency of transmitting and using power that is provided from an energy transmitting reader to an isolated, remotely powered, remotely interrogated, remotely programmed, or remotely controlled device such as a sensor transponder. The improved efficiency of transmitting power is achieved by tuning receiver and transponder coils or antennas to the same resonance frequency and by impedance matching the load using a tapped coil or a capacitive divider as more fully described below.

The improved efficiency of using power is accomplished by such approaches as integrating electronics into a low power microcontroller, using switched reactance communication instead of an RF transmitter, and turning on power using components only when needed.

The present invention also provides a way to power a high-energy consuming device that may use much more power than can be transmitted. In this case transmitted power is gradually stored in a storage device, such as a battery or storage capacitor. When enough energy has been stored in the storage device the high-energy consuming device can then be operated briefly.

The present invention also provides a more mechanically reliable hermetic seal for such a container by eliminating the potentially leaky feed-through normally required for an antenna for radio frequency external communication. This allows the device to be more reliably used in locations such as biomedical implants where fluids may leak in harming the device or where materials from the device may leak out, harming the patient or other living organism. The present inventors found that they could transmit into a sealed metal container without a feed-through or external antenna by providing the electromagnetic signal from the reader at a frequency low enough to penetrate through the metal of the container.

The present invention also provides a more mechanically robust device by eliminating mechanically sensitive parts, such as clock crystals for a microprocessor. This allows the invention to be used in adverse locations, such as in jet engines that experience high G forces.

In addition to eliminating a crystal, the present invention allows eliminating a transmitter for communicating with a sensor transponder. It also takes advantage of microprocessors that integrate separate components such as an a/d converter or a multiplexor, thereby reducing power drawn.

The present invention allows using a simple receiver coil both for harvesting energy from a remote reader that is transmitting an electromagnetic signal and for transmitting sensor data back to the remote reader. Substantial energy savings result from eliminating an RF transmitter from the sensor transponder and replacing it with switched reactance transmission. A microprocessor is used for timing and aid conversion as well as for controlling a switchable reactance for communicating sensor data from the receiver coil to the reader. Thus, the present invention provides remote powering and remote interrogation of the sensor with very little energy. It also permits communicating data into the sensor transponder, for example for remote programming of its microcontroller.

One embodiment of the invention includes a sensor, a microprocessor with on-board a/d converter, a coil, and a switched reactance. It may also include an amplifier to boost sensor output if it is low, and a multiplexor so that more than one sensor can be connected to a single microprocessor. While this is enough for communication from the sensor transponder, additional hardware could also be provided to sense external modulation, allowing two way communication. No battery or other source of on-board power is needed for powering the sensor or for the one or two-way communication, allowing the invention to be implemented in locations where replacing or recharging batteries is difficult. As mentioned above, the invention is also applicable in locations where the sensor transponder must be hermetically sealed in a metal container and a feed through to an external antenna is undesirable.

In the present invention power received by on-board receiver antenna or receiver coil 34' is converted to direct current in rectifier 50 and voltage regulator 52 to power electronic circuits that use more power than RFID systems. Sensor transponder 48 of the present invention includes receiver coil 34', microprocessor 54, multiplexor 56, amplifiers 58, and sensors 60, as shown in FIG. 2a. Sensors 60 can include sensors with a Wheatstone bridge, such as DVRT sensor 60', as also shown in FIG. 3.

Figure 3:
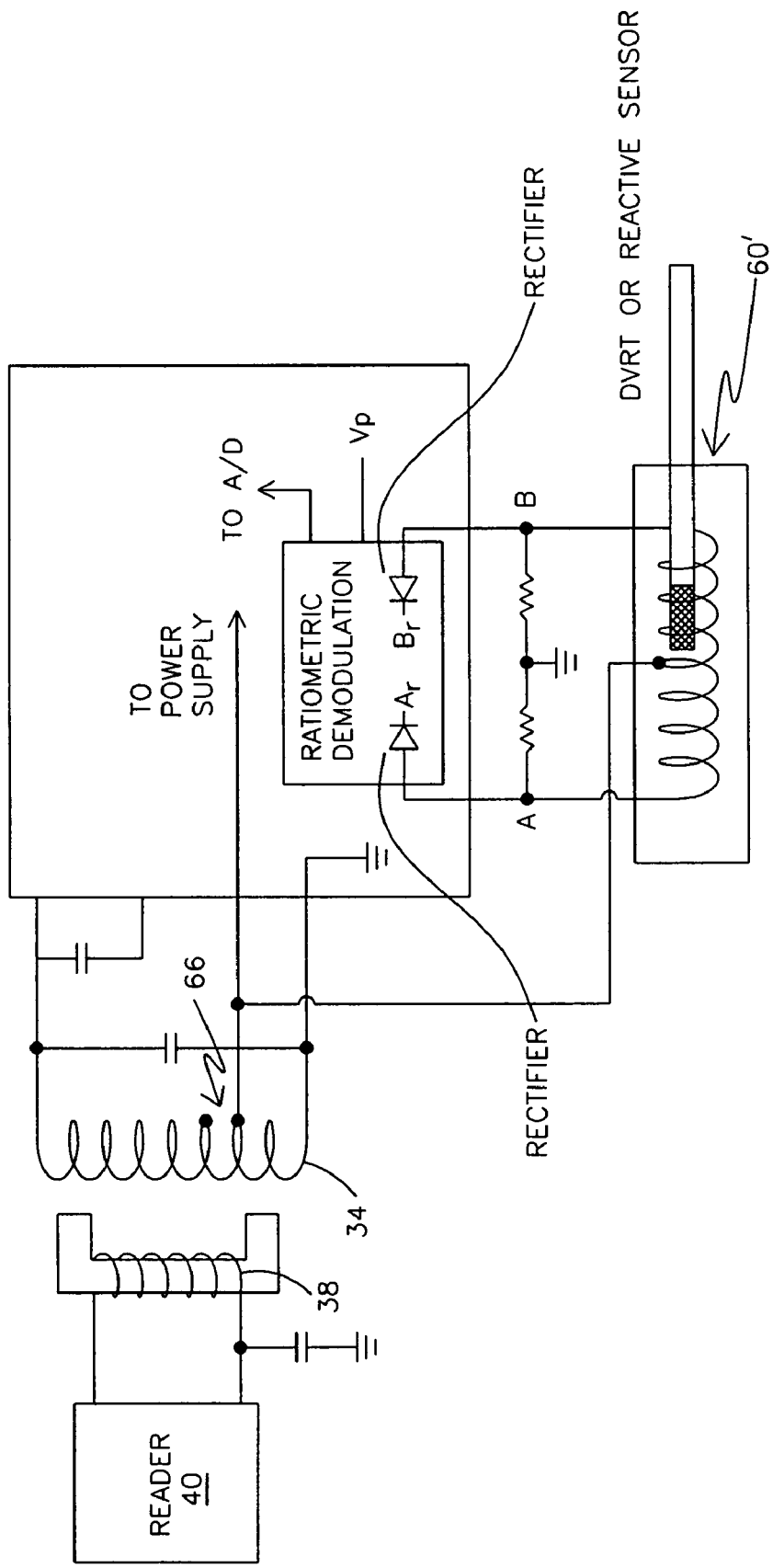
FIG. 3 is a circuit diagram of a reader and a DVRT transponder of the present invention with ratiometric signal conditioning.

Sensors, such as DVRT sensor 60', can also be powered directly by providing some of the AC power from receiver antenna or receiver coil 34', as shown in FIG. 3. Power transfer is facilitated by having both radiating interrogation reader coil 38 and receiver coil 34' tuned to resonance at the same frequency provided by oscillator 153 in reader 40 (see FIG. 9a) that sets the frequency of this AC power. Receiver coil 34' or reader coil 38 can be tuned by adjusting inductance or capacitance of the tank circuit in which they are each located. Inductance can adjusted by shorting out a portion of the coil or by switching in additional turns of a coil. Capacitance can be adjusted by such methods as switching in an additional capacitor, by shorting out an existing capacitor, by using a mechanically tunable capacitor or inductor, or by varying potential applied to an electronically tunable capacitor, such as a variable capacitance diode.

Figure 4:
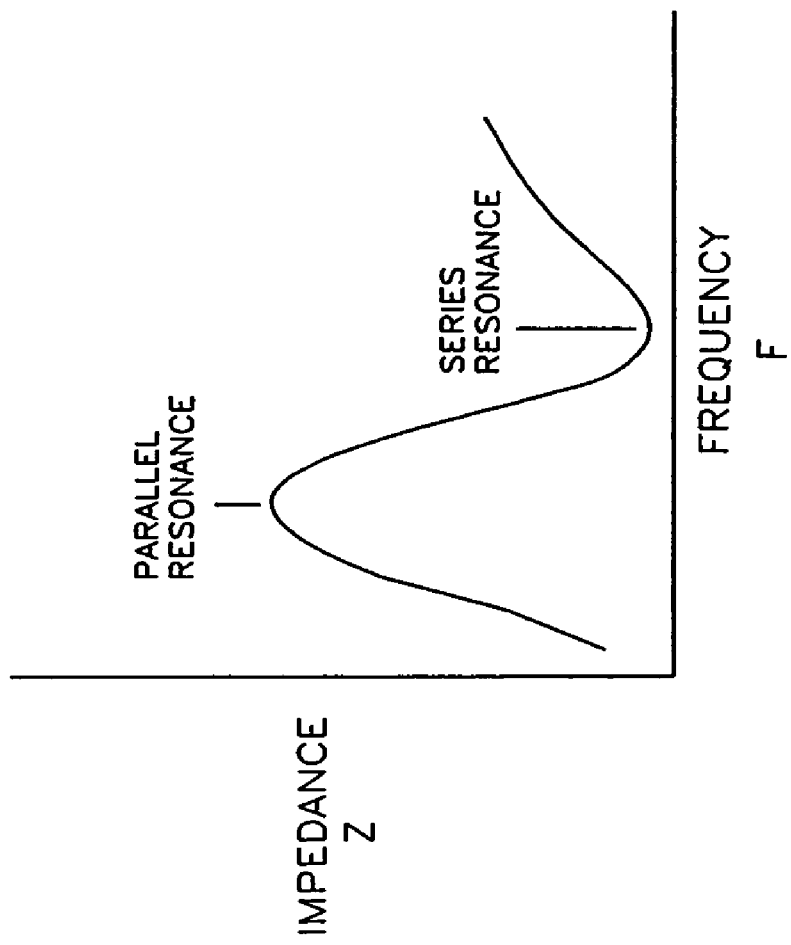
FIG. 4 is a graph showing how impedance varies with the frequency of radiation applied to a resonant tank circuit and showing the circuit absorbing a high amount of the radiation when a frequency of radiation is provided at its series resonance and showing the circuit reflection a high amount of the radiation when the frequency of the radiation is provided at the circuit's parallel resonance.
Figure 5:
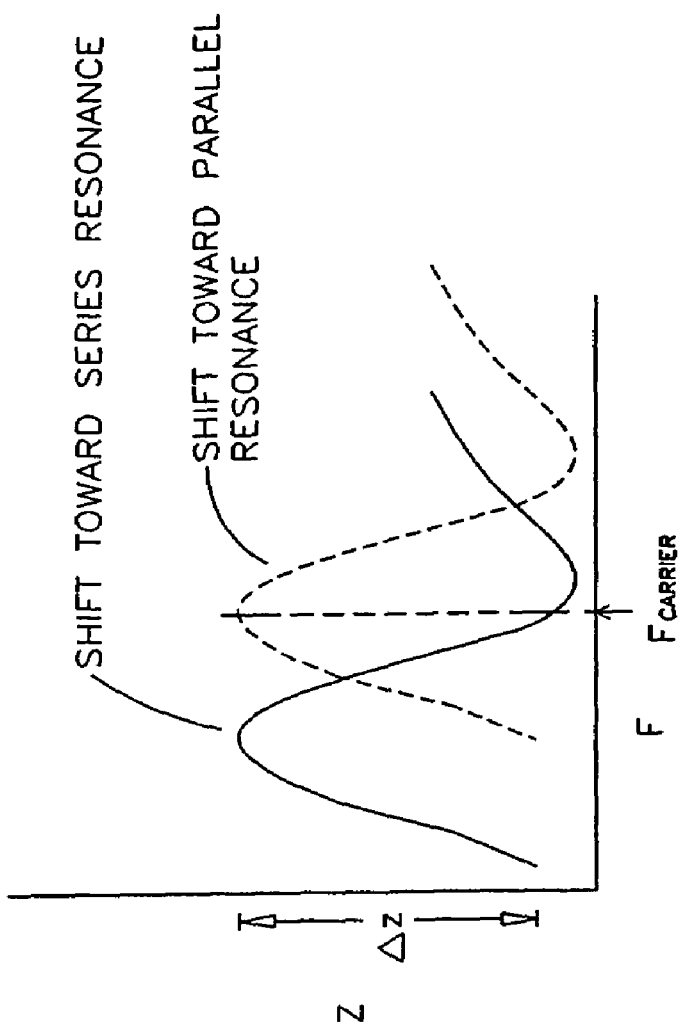
FIG. 5 is a graph showing that a large impedance shift results from switching a reactance into a resonant tank circuit having a high Q.

The impedance across a resonant tank circuit, such as tank circuit 28' of FIG. 2a, is shown in FIG. 4. Communications from remote powered switched reactance sensor transponder 48 to reader 40 is accomplished by taking advantage of this change in impedance with resonance frequency. Shifting the resonance of receiver coil 34' slightly toward series resonance or toward parallel resonance, as shown in FIG. 5, provides a substantial change in power drawn by receiver coil 34', changing the loading on reader coil 38. In series resonance receiver antenna or coil 34' can be said to be in an absorptive state where it places a heavy load on reader coil 38, reducing the Q of its resonance and reducing the voltage across it. When tuned to parallel resonance receiver coil 34' can be said to be in a reflective state where it reduces the load on reader coil 38, raising the Q of its resonance and increasing the voltage across it. Shifting the reactance of receiver coil 34' in this manner induces a detectable voltage amplitude shift on reader coil 38, which can be converted to data in reader 40 with methods described below.

Coil 34 can be a spool type coil or it can be patterned on a plane. For patterning in a plane it can be formed on a surface, such as a plastic surface. It can mounted on a PC board or it can be an external coil electrically connected to components on a PC board. If external, its shape can be modified to allow a larger coil to be used for the available space.

Instead of varying reactance by switching a capacitor in and out of tank circuit 28 it is also possible to vary reactance by providing a way to change inductance of receiver coil 34. One way to change inductance of receiver coil 34 is to provide a switch with wires making contact to receiver coil 34 at two positions so that a portion of coil 34 is shorted out when the switch is closed. Inductance and reactance of coil 34 would be reduced when the shorting switch is closed and elevated to the coil's full value when the switch is open. Alternatively, a second coil could be switchably included in tank circuit 28.

Power Transfer and Power consumption

As mentioned above, one problem with using remotely powered switched reactance communications with sensors, actuators or other active digital telemetry systems has been their increased power consumption relative to prior art traditional RFID tags. This increased power consumption is due to the more complex electronics and the power requirements of the active sensors involved. The present inventors recognized that since switched reactance communications is dependant on the Q of the resonance of both antennas or coils 34' and 38, connecting a circuit that draws significantly higher power than an RFID tag across the whole transponder coil 34' causes the Q of this resonance circuit to go down to the point where communications is difficult. Since Q=R/X for a parallel resonant tank circuit, where X is the reactance and R is the resistance, the Q depends on the load resistance across it, and the greater the resistance in parallel with the coil, the greater the Q factor. The circuit being powered by coil 34' provides that parallel resistance. The more current it draws, the lower that resistance in parallel, and the more in drags down the Q factor. However, the present inventors found that by instead providing that resistive load at low impedance tap 66 in coil 34', located to match the low resistance of the transponder circuit load from sensors 60, 60', the Q factor of full coil 34' is preserved. Power is thus more efficiently transmitted to coil 34' and also more efficiently transferred from coil 34' to the load. The Q factor of reader coil 38 is also kept high using this tapped coil scheme.

Figure 6:
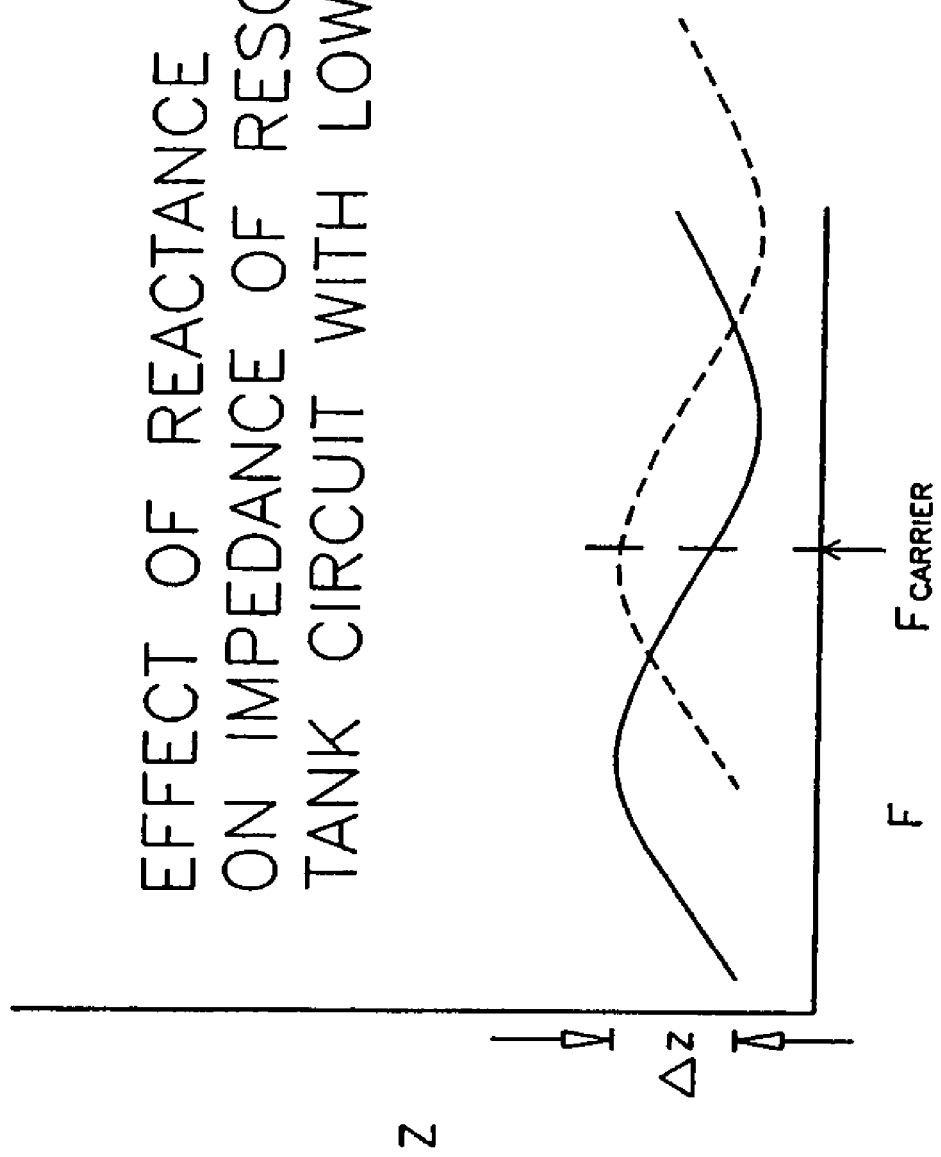
FIG. 6 is a graph showing that a small impedance shift results from switching a reactance into a resonant tank circuit having a low Q.

A comparison of FIGS. 5 and 6 shows that shifting the resonance of a low Q tank circuit produces a smaller change in impedance ΔZ than the shift with a high Q tank circuit. In either case that change in impedance is detected by reader coil 38 as data. However, if those changes in impedance are small, as in FIG. 6, then the signal is smaller and detection of the change in impedance is more difficult. Thus, the resultant shifts in voltage amplitude of the reader coil are much lower and the signal is more difficult to detect when receiver transponder coil or receiver antenna 34' has a low Q. The present invention preserves the high Q and thus preserves the higher more easily detectable signal at reader 40.

The present inventors recognized that advantage could be obtained by more efficiently getting power into transponder receiver coil or receiver antenna 34' as well as by better managing power consumed by sensors 60, 60'. As described above, the present inventors recognized that they could more efficiently use the coupled AC power by matching the impedance of switched reactance circuit 30 at receiver transponder coil 34' using tap 66, as shown in FIG. 2a. Providing tap 66 leaves the Q of total coil 34' high so it continues to receive power from reader coil 38 with high efficiency while providing a low impedance source of AC power for the sensor circuit. In addition, the present inventors found that providing multiple taps 66, connection could be accomplished that more finely matched to a varying load, to multiple loads, or to a network of loads.

Receiver transponder coil 34' connected to different sensors may experience different power requirements depending on sensor current draw. The present inventors recognized that a plurality of taps 66 could be provided on receiver transponder coil 34' to dynamically optimize the impedance matching by using sensor channel input to MUX 56 on Vp line 67 to monitor the available voltage and to select appropriate tap 66 with switch 68 controlled by microprocessor 54, as also shown in FIGS. 2a–2c. In these embodiments of the invention sensor transponder circuit 48a–48c can more effectively switch the reactance of coil 34' because the requisite high Q of tank circuit 28' is even better preserved, while delivering several milliamperes to power transponder circuit 48a–48c.

Power consumption can be further reduced by multiplexing the DC excitation to sensors using MUX 69 to provide Vcc power to one sensor at a time, as shown in FIG. 2a. When used in combination with dynamically switched plurality of taps 66, high Q and efficient power transfer are very well maintained.

Alternatively, tap 66 can be replaced with capacitive divider 66', as shown in FIG. 2d. Capacitive divider 66' includes capacitors, one or more of which can be varied electronically to dynamically impedance match the output to a load.

Elimination of Crystals

Further improvement is available by eliminating oscillator crystals in receiver transponder 48a–48c. Crystals are a relatively bulky and are mechanically delicate. RFID tags avoid using crystals by instead using the frequency of the AC interrogation signal for system timing. In RFID tags this is acceptable but for applications, such as sensor transponder 48a–48c, it is easier to manage system design optimization when system timing and excitation frequencies are independent of one another. Independent frequencies allows the system to be frequency agile—the system can accommodate different antenna or coil geometries required by different applications. For example, low excitation frequencies can be provided, allowing radiation from reader 40 to penetrate through metal walls of hermetically sealed containers but fast system timing can still be used if the system timing is independent of the excitation frequency.

Crystals can be eliminated from the circuit while still providing independent system timing by using control processor 54 with integrated RC oscillator clock circuit 70. While this is disadvantageous compared to a crystal for initial accuracy of system timing and drift of system timing with temperature, the present inventors found that A/D converter sample timing and the timing of other software functions are not critical.

They found, however, that accurate system timing is desirable for maintaining accurate baud rates in serial communications. They found that asynchronous serial format data works best if data rate variation is maintained within 1% for serial ports but an RC clock cannot usually maintain that 1% tolerance over typical ambient temperature changes.

The present inventors found that with a well known data encoding method that embeds the baud rate clock in the data stream, such as Manchester or bi-phase encoding, and with a microprocessor controlled receiver at the reader, the clock and data can be recovered in a manner that will tolerate more than a 10% variation in data baud rate with negligible effect on Bit Error Rate (BER). They found that this ten percent communications timing accuracy is easily achieved over the 150 degrees Celsius operating temperature range in the remote powered telemetry system with RC based timing. These data can then be sent by the smart reader to a host computer using accurately timed standard serial communications. This system topology has the further advantage of supporting protocol conversion at the reader, which allows these remotely powered transponders to be integrated into other systems, such as MicroStrain's Wireless Web Enabled Sensor Network (WWSN).

Figure 7:
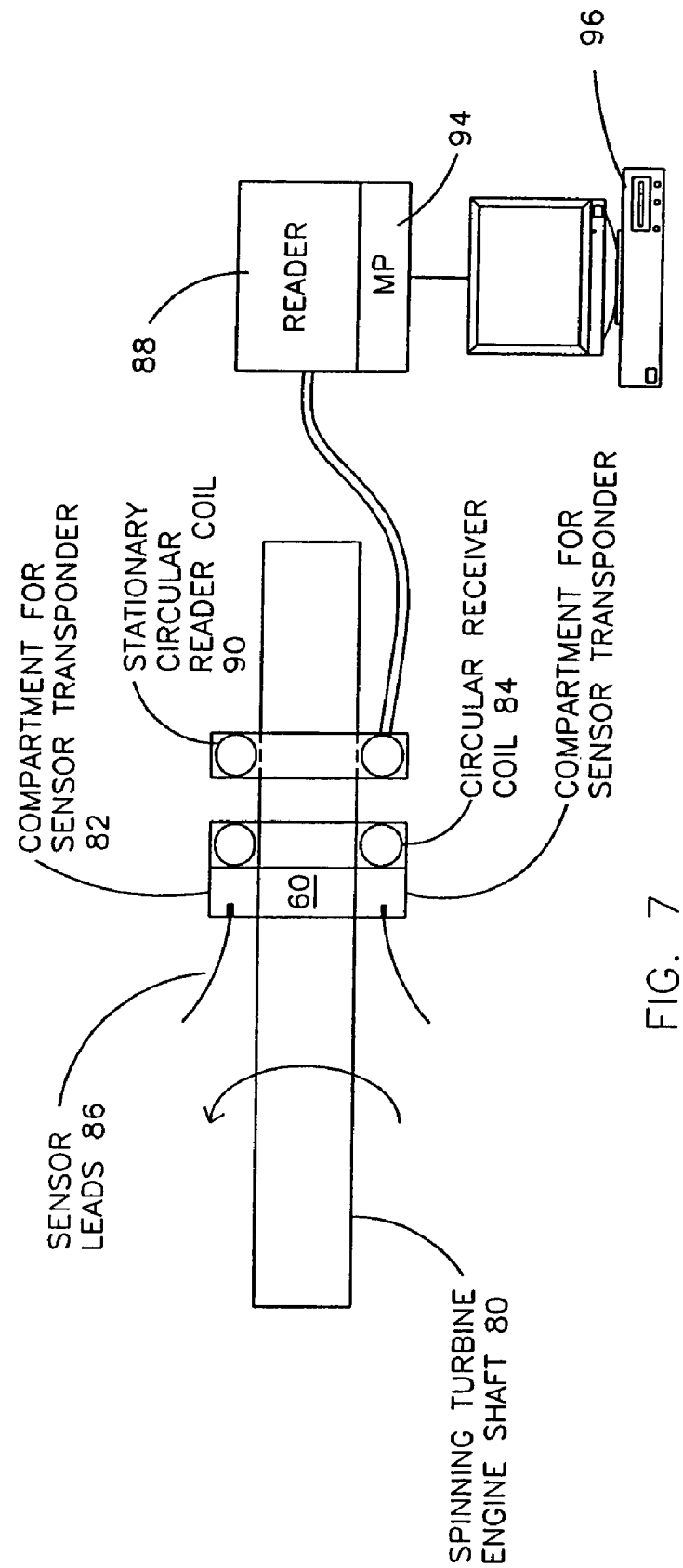
FIG. 7 is a schematic block diagram of a jet engine with a rapidly spinning turbine shaft to which is attached a sensor transponder of the present invention while a non-rotating reader reads data from a switched reactance in the spinning transponder.

In addition to allowing packages to be smaller, the elimination of the crystal from the remotely powered transponders also improves compatibility with high 'G' force environments. High G force environments are found in jet engines where spinning turbine 80, as shown in FIG. 7, can generate forces as high as 95,000 G's. Crystals will fracture when exposed to a few hundred G's whereas a properly encapsulated system with RC based timing has been demonstrated to survive more than 90,000 G's centrifugal force. The present invention allows sensors mounted on such a spinning turbine to be read to provide measurement of temperature, strain, and other parameters.

As shown in FIG. 7, sensor transponder 82 and receiver coil 84 are mounted to spinning shaft 80 and spin with shaft 80. Sensor leads 86 from sensor transponder 82 extend to various parts of spinning turbine 80 where sensors 60 are mounted. Sensors 60 can be thermocouples, strain gauges, pressure transducers, or other sensors. Reader coil 88 is mounted around spinning shaft 80 to inductively provide power to sensor transponder 82 and to read data from sensor transponder 82.

Receiver coil 84 includes tap 66 (see tap 66 in FIGS. 2*a*–2*c*) to preserve the high Q of receiver coil 84 during operation of sensor transponder 82. No crystals are provided on sensor transponder 82. Instead RC oscillator clock circuit 70 is provided in sensor transponder 82 (see FIG. 2*a*). Manchester or biphase encoding is also used in sensor transponder 82 to transmit clock rate data along with sensor data, allowing reader 88 connected to reader coil 90 to track the drifting data rate from transponder 82 and extract the timing from the train of modulation it receives. Microprocessor 94 in reader 88 is connected to host computer 96. Microprocessor 94 converts the Manchester or biphase data received from transponder 82 to asynchronous data for transfer to host computer 96.

In the present invention switchable tap 66 provides efficient transfer of power from reader coil 88 to receiver coil 84. Switchable tap 66 also provides improved communications by maintaining high quality factor Q. Crystal elimination allows sensor transponder 82 to function in a high G jet engine environment while simplifying the circuit and allowing it to be smaller. The Manchester or biphasic encoding allows clock recovery from a potentially drifting RC oscillator, facilitating crystal elimination. The combination of these three elements has significant advantage in receiving power, transmitting data, reducing size, improving resistance to G forces, and extracting timing information.

Similarly, in a biomedical application switchable tap 66 and the elimination of crystals allow substantial size reduction as well as reducing power consumption and communication out from the transponder. Manchester or biphasic encoding also provides for correction for change in temperature. These elements can be used with sensors, power management of sensors, and shunt calibration of sensors to allow making measurements in difficult environments, such as high G or biomedical applications, where they could not be made before.

Communication with a Sensor in a Metal Enclosure

Figure 14:
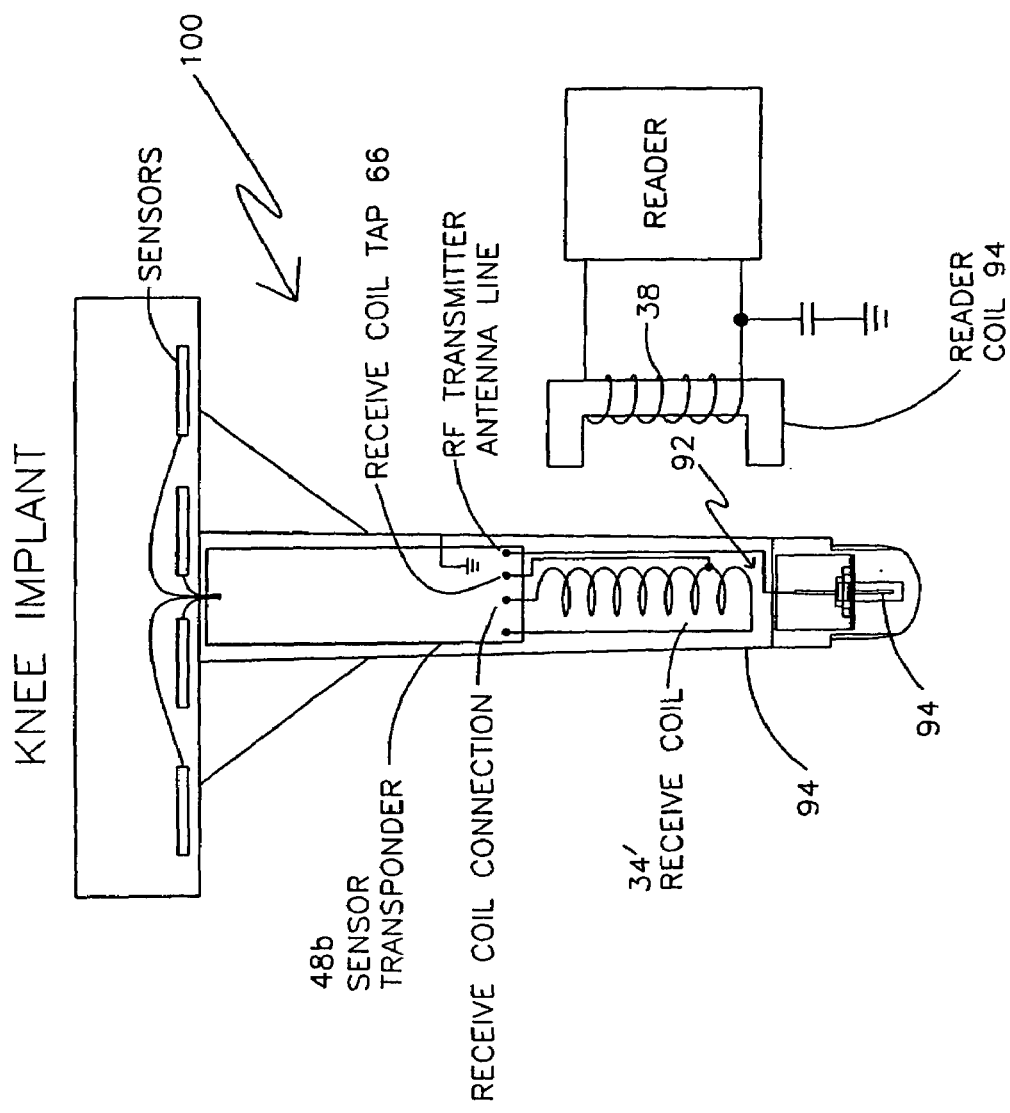
FIG. 14 is a schematic block diagram of a knee implant showing a sensor transponder in a hermetically sealed container with an RF transmitter, a feed-through and an antenna for external transmission of sensor data to a reader.

With hermetically sealed metallic enclosure 72, feedthrough 92 connecting to antenna 94 can be used when RF transmitter 96 is included with sensor transponder 48*b* in enclosure 72, as shown in FIG. 2*b*. Smart knee implant 100, as shown in FIG. 14, provides an example of such a hermetically sealed package 72 with such a feed-through 92 and such an antenna 94. Receiver coil 34' harvests energy from reader coil 38 as described herein below. Reader coil 34' uses this energy to power sensor transponder circuitry 48*b* and to transmit data out of hermetic package 72 by applying frequency modulated or amplitude modulated RF data to feed-through 92 which is isolated from hermetic package 72. In this embodiment only power is provided through inductive receiver coil 34'. Communications is through RF transmitter 96, as shown in FIG. 2*b*.

However, feed-throughs, such as feed-through 92, adds cost, and feed-throughs can break or leak. Therefore eliminating feed-through 92 would be highly desirable for orthopedic implants, such as knee implant 100 of FIG. 14.

Low Frequency Excitation and Elimination of FeedThroughs

The present inventors recognized that low excitation frequency provides advantage by enabling power to be transmitted through certain metals, such as those used in hermetically sealed biomedical implants, including titanium and stainless steel. Low frequency also allows switched reactance communications to be accomplished through these metals. RFID tags have been standardized on 125 kHz and on 13.565 MHz, frequencies that don't penetrate through metals very well, especially for ferrous metals. For titanium, frequencies up to one MHz can be used. The use of an insulating material has been disclosed to allow RFID tags to work near metals but not through metals. The present inventors recognized that communication to RFID tags or to transponders enclosed in metal containers could be made successful by changing the system operating frequency to a range that more efficiently passes through the metal. They found that providing low frequency radiation penetrates deeper into metal. They found that with a frequency of 44 KHz, substantial energy penetrated, and they were able to communicate with switched reactance transponders enclosed in hermetically sealed metal containers, such a titanium container.

Preferably the frequency is less than 125 kHz. More preferably frequency is in the range of tens of kHz, such as around 44 kHz. The inventors found even greater penetration through metal in one application at even lower frequency, at about 4 kHz.

Alternatively, other materials can be used to provide hermetically sealed container 72, as shown in FIGS. 2*a*–2*c*. For example container 72 can be hermetically sealed ceramic, through which high frequency radiation will pass. Or it can be non-hermetically sealed with such materials as composites, polymers, or epoxies through which high frequency radiation will also pass.

Feed-through 92 can be eliminated in the metal container embodiment of FIG. 14 by providing the low frequency signal from reader 40 into a metal hermetically sealed container 72 and by using switched reactance modulation of receiver coil 34', as shown in FIGS. 2a and 2c to communicate out through metal container 72 at this low frequency.

Receiver coil tap 66 continues to be provided to improve efficiency of delivering power to sensor transponder 98, as shown in FIG. 14.

Figure 15:
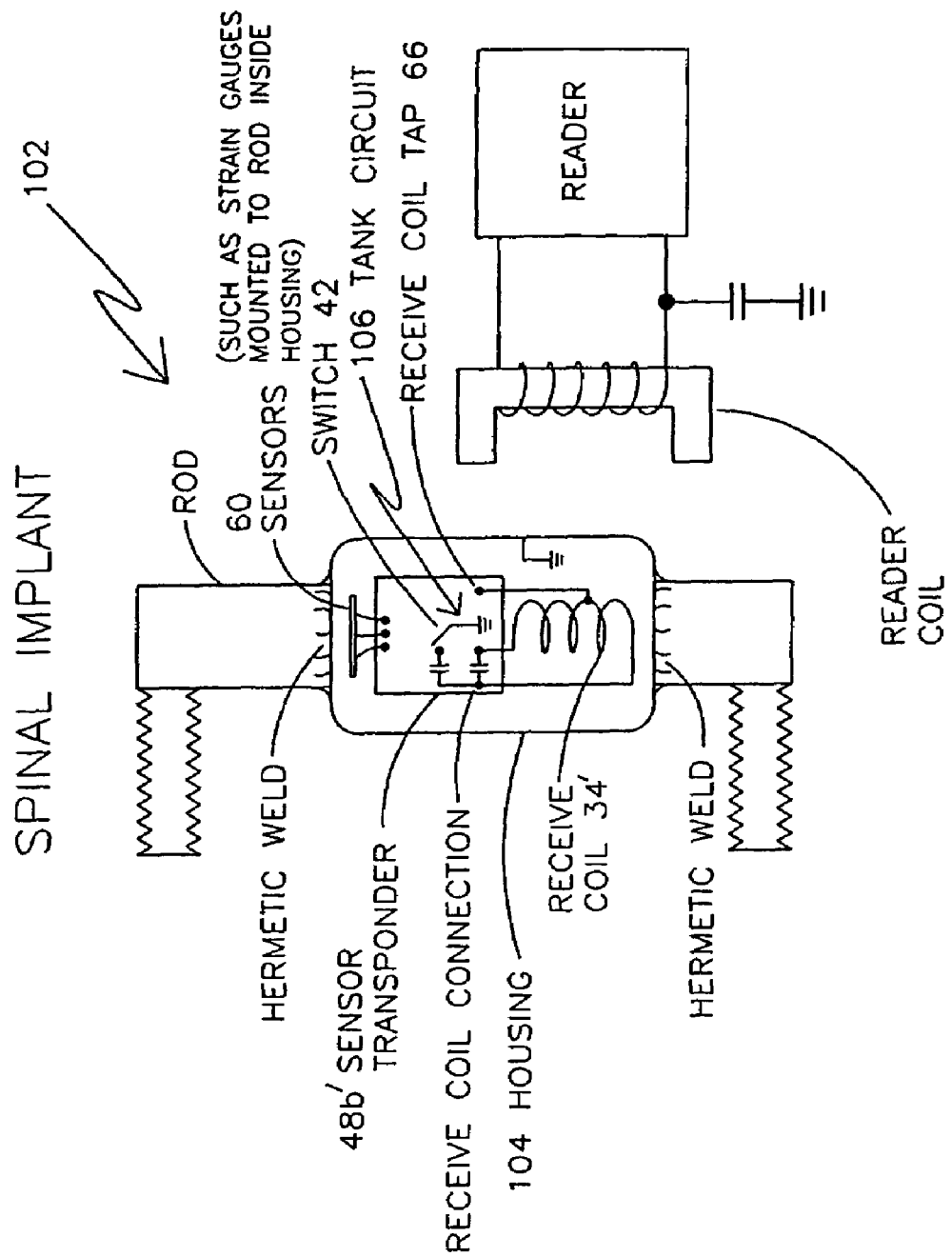
FIG. 15 is a schematic block diagram of a spinal implant showing a sensor transponder in a hermetically sealed container with a switched reactance transponder, there being no feed-through, and instead power and communication are provided through the hermetically sealed container because the reader provides a signal at a sufficiently low frequency to penetrate through the metal container.

Feed through elimination is also illustrated for spinal implant 102 of FIG. 15. Spinal implant 102 is shown with both the RF antenna and the feed-through eliminated by providing for communication through hermetically sealed metal housing 104. Such communication through metal housing 104 is achieved by providing sensor transponder 48a, 48b which includes receiver coil 34' with tap 66', switched reactance resonant tank circuit 28' with capacitor 36, switch 42, switched reactance capacitor 31, sensors 60, and other elements included in FIG. 2a, such as microprocessor 54. The antenna and feed-through can similarly be eliminated in any other implant or any other device, as shown in FIGS. 15 and 2a. Switchable tap 66 can also be provided, as shown in FIG. 2a.

Figure 16A:
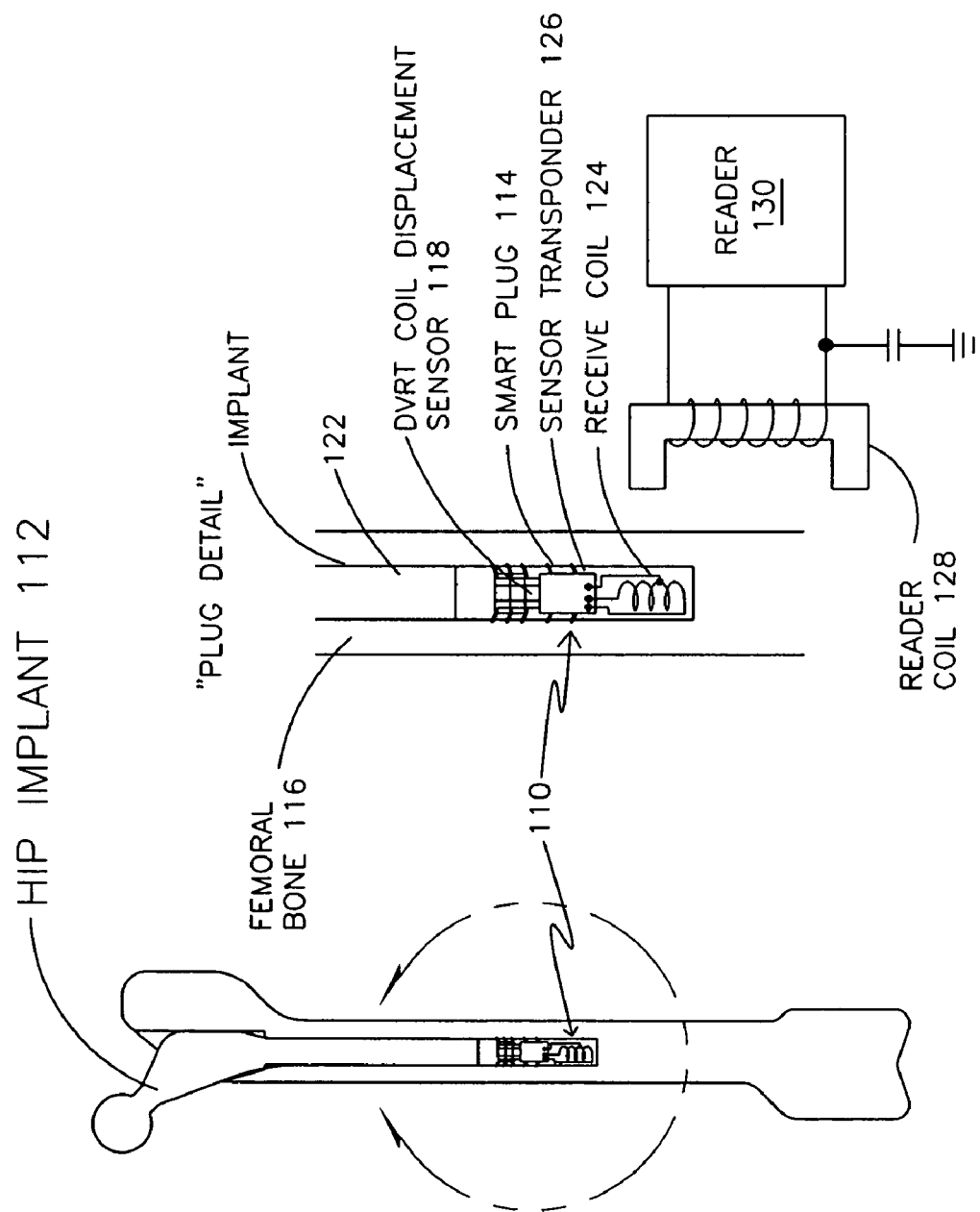
FIG. 16a is a schematic block diagram of a hip implant adjacent a DVRT in a sensor transponder smart plug that can measure movement of the hip implant and communicate that movement to an external reader.

Hip subsidence measuring device 110 for hip implant 112, shown in FIG. 16a, includes smart plug 114. Movement of hip implant 112 within femoral bone 116 is detected with DVRT 60' in smart plug 114 implanted in femoral canal 122 of femoral bone 116. The circuit of FIG. 2a with a DVRT as sensor 60' as implemented in FIG. 3 is used in this device. Output of DVRT 60' is digitized and used to modulate receiver coil 124 of sensor transponder 126. This modulation is detected by reader coil 128 of reader 130, located outside the body, to detect the position of hip implant 112 with respect to DVRT 60' located in smart plug 114. Early detection of subsidence or movement of hip implant 112 is helpful because subsidence is an indication of loosening of hip implant 112 that can become a clinical problem a number of years later. So this type of device can be used to compare various hip implants and determine which is best. Hip implant 112 is located in hermetically sealed container 130 and communication to hip implant 112 through its metal walls is accomplished using switched reactance sensor transponder 126 operating at low frequency.

Figure 16B:
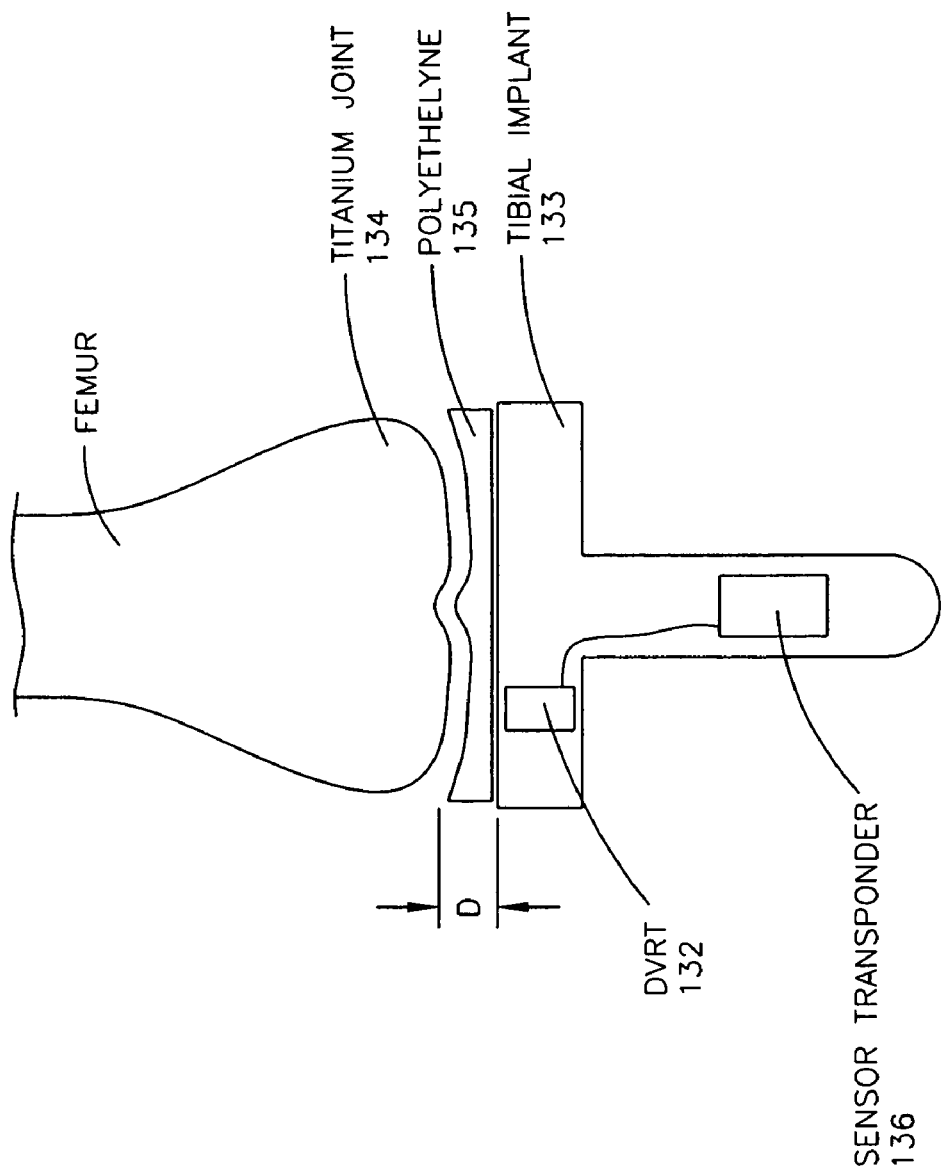
FIG. 16b is a schematic block diagram of a knee implant for measuring wear of a polyethylene bearing surface with a non-contacting DVRT.

In another embodiment, an implant may involve two components, one to measure movement of the other. For example, non-contacting DVRT 132 may be located in one of the implants 133 and used to measure the distance D to the other implant 134, as shown in FIG. 16b. The implants may be across a joint, such as a knee or hip joint. In these applications polyethylene component 135 is used to provide a low friction articulation between the two components and across the joint. However, polyethylene component 135 may be subject to wear, and this will result in the two components becoming closer to one another. This relative change in position can be detected by DVRT coils 132 which in turn can be monitored by sensor transponder 136. This wear detection information would be helpful to clinicians and therapists charged with the care of patients having artificial knees and hips. Non-contacting DVRTs are available from Microstrain, Inc, Williston, Vt. A similar technique can be used for wear detection in other apparatus, such as friction or cold flow based wear.

Figure 17A:
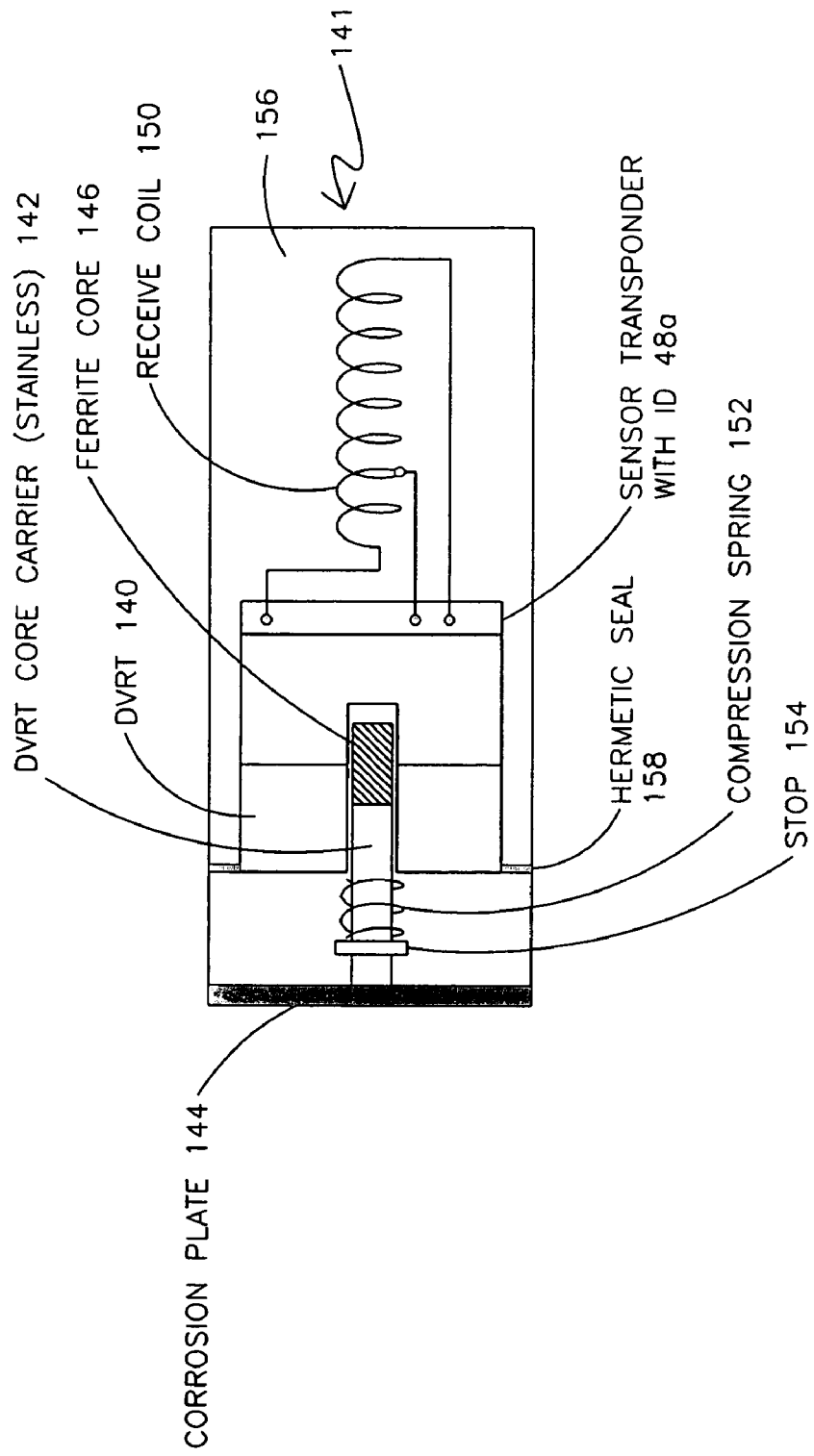
FIG. 17a is a schematic block diagram of a hermetically sealed remotely powered and remotely interrogated corrosion measuring DVRT system with a spring element.

DVRT 140 can also be used in corrosion detection device 141 in which spring loaded DVRT core carrier 142 can break through metallic element 144 once metallic element 144 corrodes away, as shown in FIG. 17a. DVRT core carrier 142 includes ferrite core 146. Movement of DVRT core carrier 142 and its ferrite core 146 as a result of corrosion of corrosion plate 144 changes reactance of DVRT 140. That change in reactance is detected by sensor transponder 148 and this data can be transmitted out by receiver coil 150. DVRT core carrier 142 is fabricated of a material, such as stainless steel. Compression spring 152 pressed against stop 154 provides spring loading for DVRT core carrier 142. Container 156 is sealed with hermetic seal 158, and receiver coil can transmit through hermetically sealed container 156, as described herein above.

Figure 17B:
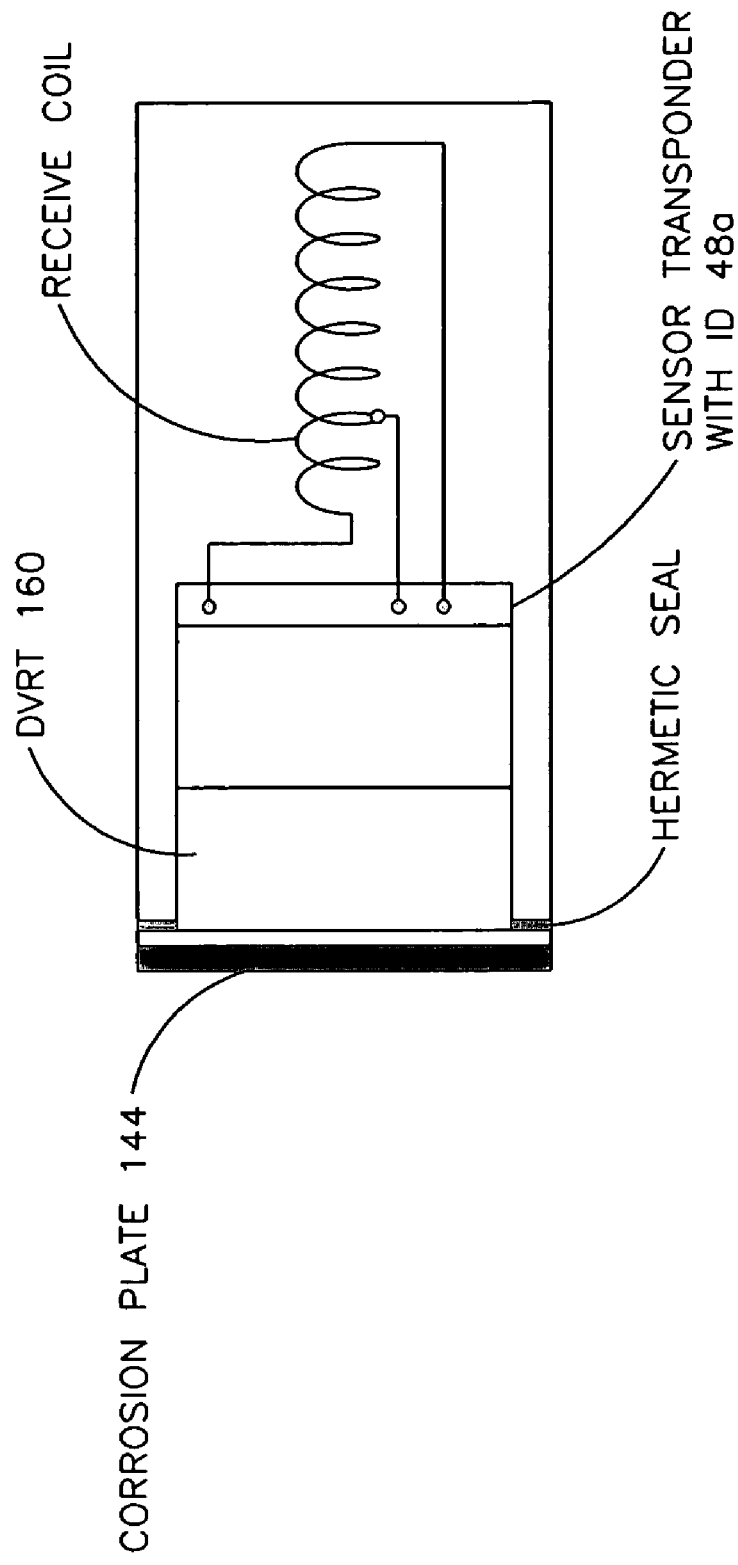
FIG. 17b is a schematic diagram of a hermetically sealed remotely powered and remotely interrogated corrosion measuring DVRT system with no spring element.
Figure 17C:
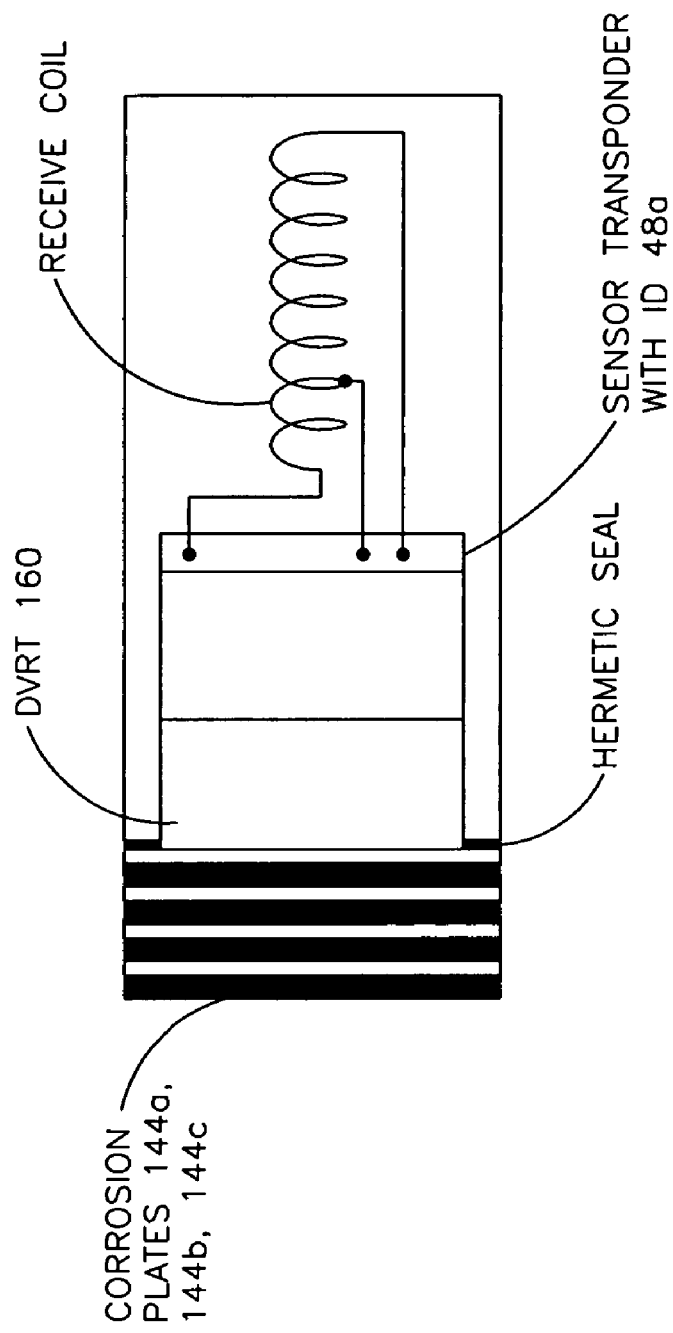
FIG. 17c is a schematic diagram of a hermetically sealed remotely powered and remotely interrogated corrosion measuring DVRT system with no spring element for measuring corrosion of a stack of corrosion plates.

Corrosion detection device 170 can include stack of corrosion plates 144a, 144b, 144c made of a number of metallic elements subject to corrosion, each with different thickness, wherein each stack of plates 144a, 144b, 144c has its own spring loaded DVRT and each sensor transponder has a unique address, as showing for one such stack of corrosion plates and one such DVRT in FIG. 17c. When interrogated, the corrosion rate can be estimated by determining at which addresses corrosion sufficient for the DVRT to break through each plate of the stack of corrosion plates is found and which addresses do not have sufficient corrosion for break through. Such devices can be embedded along with rebar in concrete, for example, to allow condition based maintenance of structures made from concrete in which the rebar is subject to corrosion.

Figure 17D:
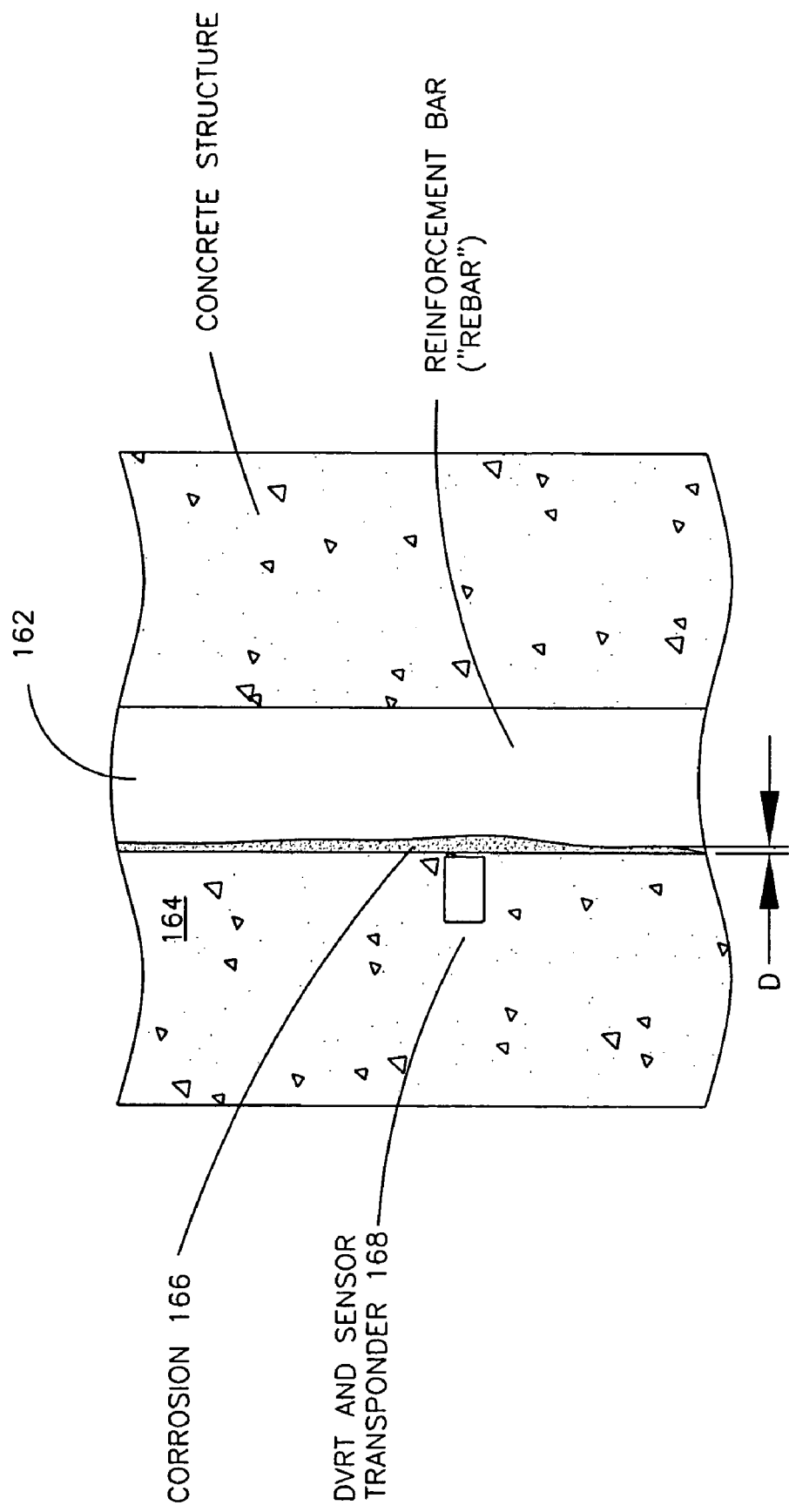
FIG. 17d is a schematic diagram of a system for measuring corrosion of reinforcement bar in concrete with a non-contacting DVRT.
Figure 17E:
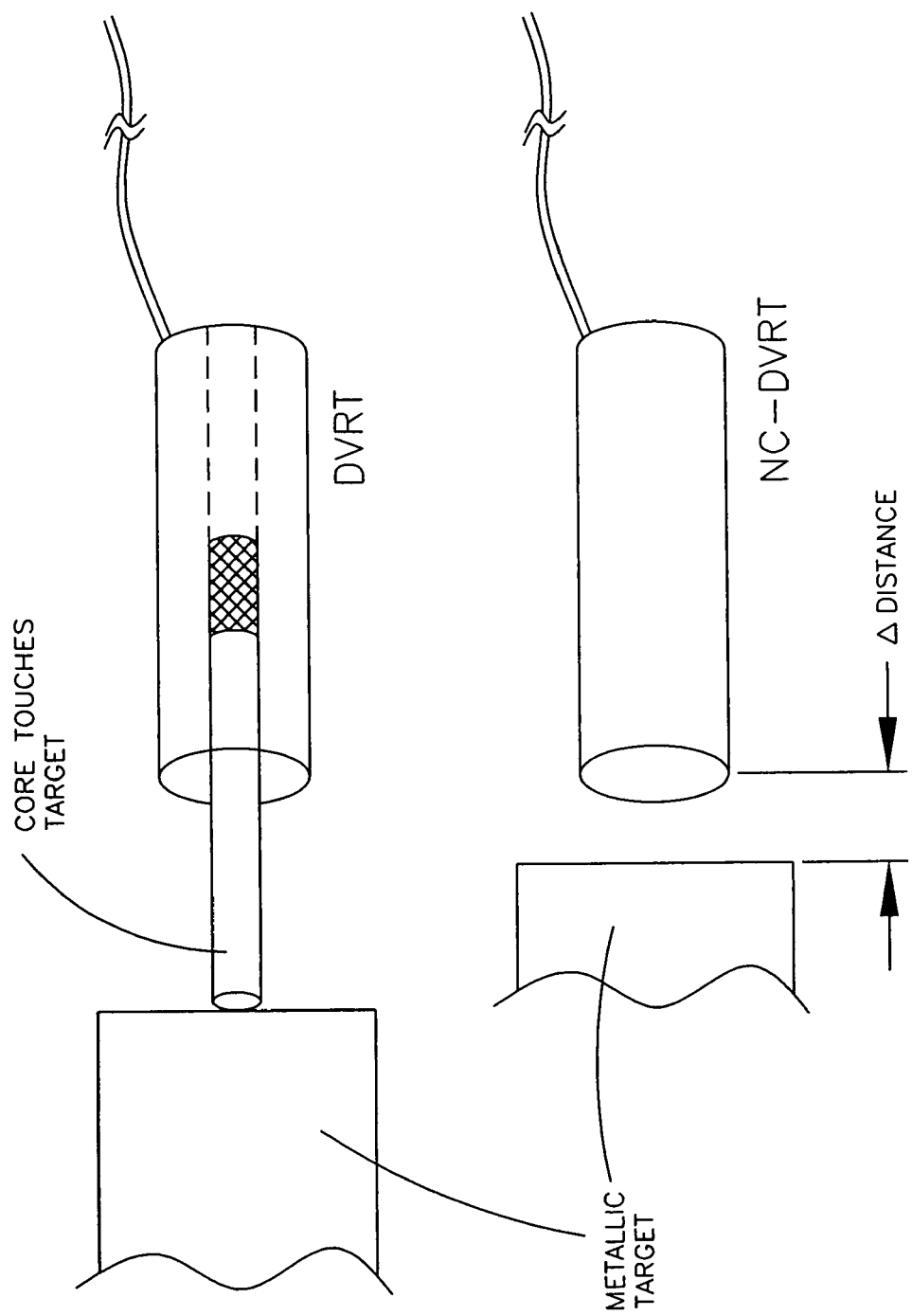
FIG. 17e is a schematic diagram comparing operation of a non-contacting DVRT with a contacting DVRT.

Alternatively output data of a DVRT will gradually change with corrosion of a metal layer, as shown in FIG. 17d. In this case reinforcement bar 162 in concrete 164 is subject to corrosion 166. As rebar 162 rusts the distance D between embedded DVRT sensor transponder 168 and metal of rebar 162 increases, and that increase in spacing D is detected by DVRT sensor transponder 168 and transmitted from DVRT sensor transponder 168. A more detailed view of non-contacting DVRT 160 measuring the corrosion of a metallic element 144 without a spring and without movement of a core, is shown in FIG. 17b. A comparison of the workings of contacting and non-contacting DVRTs is shown in FIG. 17e.

Figure 18:
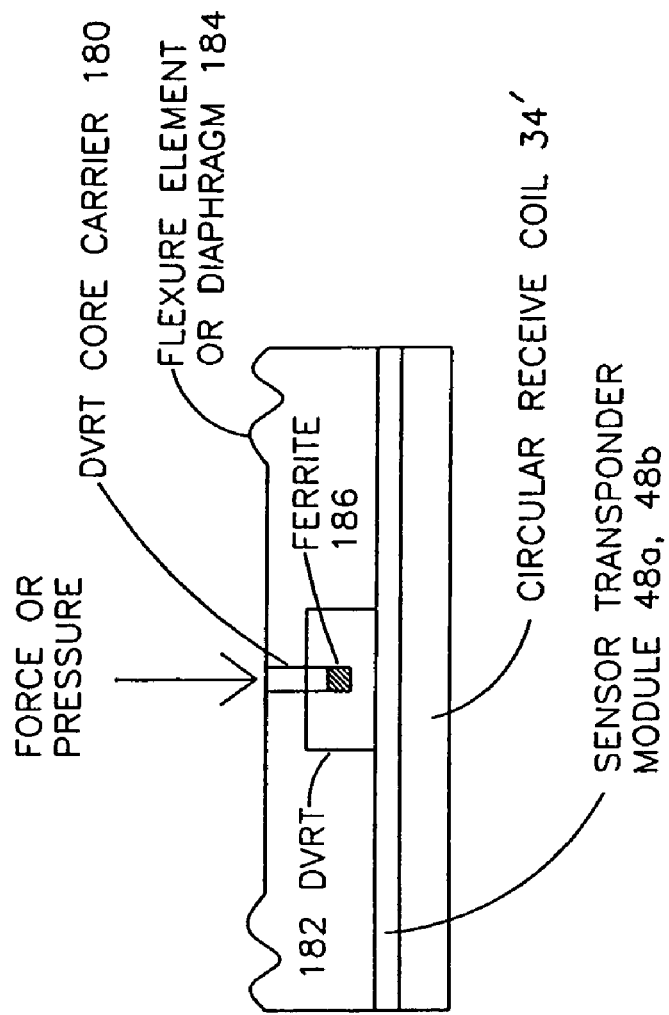
FIG. 18 is a schematic diagram of a remotely powered and remotely interrogated DVRT for force or pressure measurement.

In another embodiment DVRT core carrier 180 of DVRT 182 is connected to hermetically sealed flexure element 184, as shown in FIG. 18. Core carrier 180 contains ferrite core 186. Flexure element 184 responds to force or pressure, pushing in or pulling out core carrier 180 of DVRT 182 with it as it moves. As ferrite core 186 moves, inductance of DVRT 182 changes, and this change in inductance is measurable by electronics connected to DVRT 182 and can be transmitted externally using switched reactance circuit in sensor transponder 48a, 48e and receiver coil 34' as shown in FIG. 18 and FIGS. 2a, 2c. DVRT 182 thus provides a measure of the force or pressure on flexure element or diaphragm 184.

A book, *Biomedical Telemetry* by R. McKay describes an analog device using coils and a diaphragm to measure forces and pressures within a live body. It describes transmitting the data out of the body using an RF transmitter powered by an implanted battery. The present invention improves upon this scheme by providing power to a digital sensor transponder through a sealed metal container. By providing a tapped coil, a microprocessor and an a/d converter, it provides a digital system that has higher measurement resolution and the ability to perform error checking.

Figure 19:
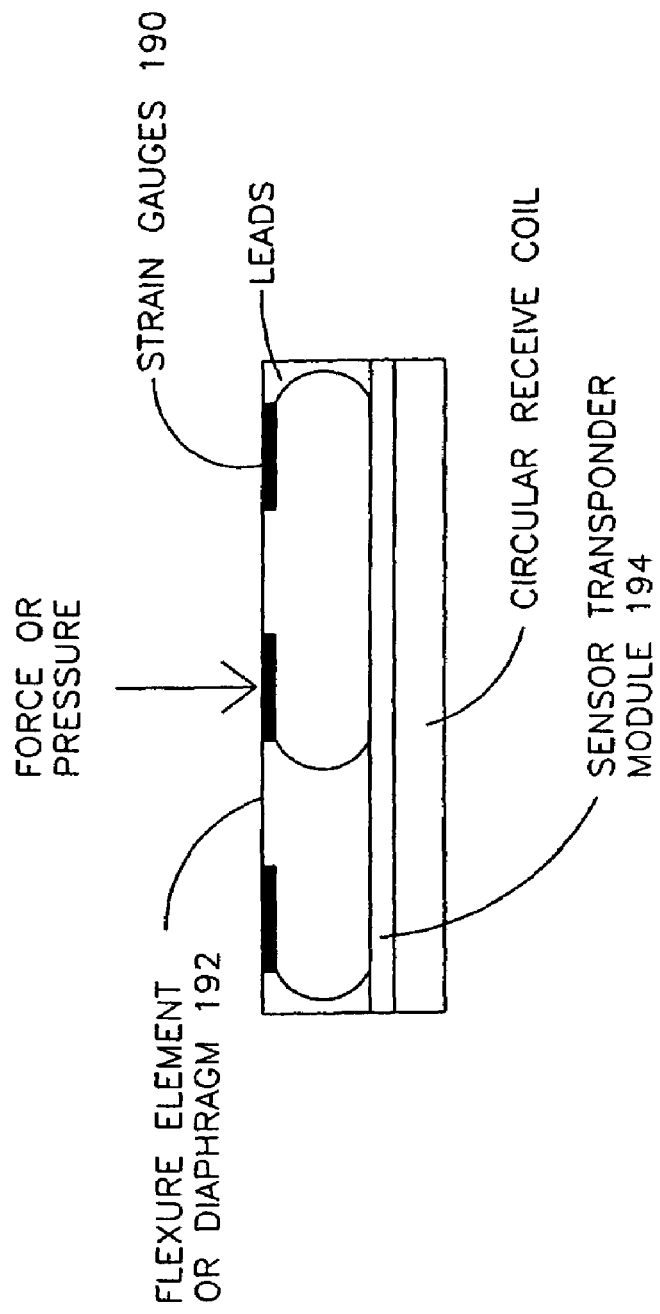
FIG. 19 is a schematic diagram of another embodiment of a remotely powered and remotely interrogated strain gauge for force or pressure measurement that uses a flexure element or diaphragm.

In another embodiment strain gauges 190 are bonded to or deposited onto flexure element 192, as shown in FIG. 19. These strain gauges 190 are connected to sensor transponder 194, which can include a circuit such as sensor transponder 48a, 48c in FIGS. 2a, 2c. They may be remotely powered and interrogated as illustrated in FIGS. 2a, 2b. Pressure imparted on flexure element or diaphragm 192 bends flexure element or diaphragm 192 and this bending is detected by strain gauges 190. The measurement from strain gauges 190 is processed in sensor transponder module 194, which is similar to sensor transponder elements 48a or 48c in FIGS. 2a, 2c, and transmitted externally using switched reactance communication, as described above.

Multiple Addressable Transponders

Figure 8A:
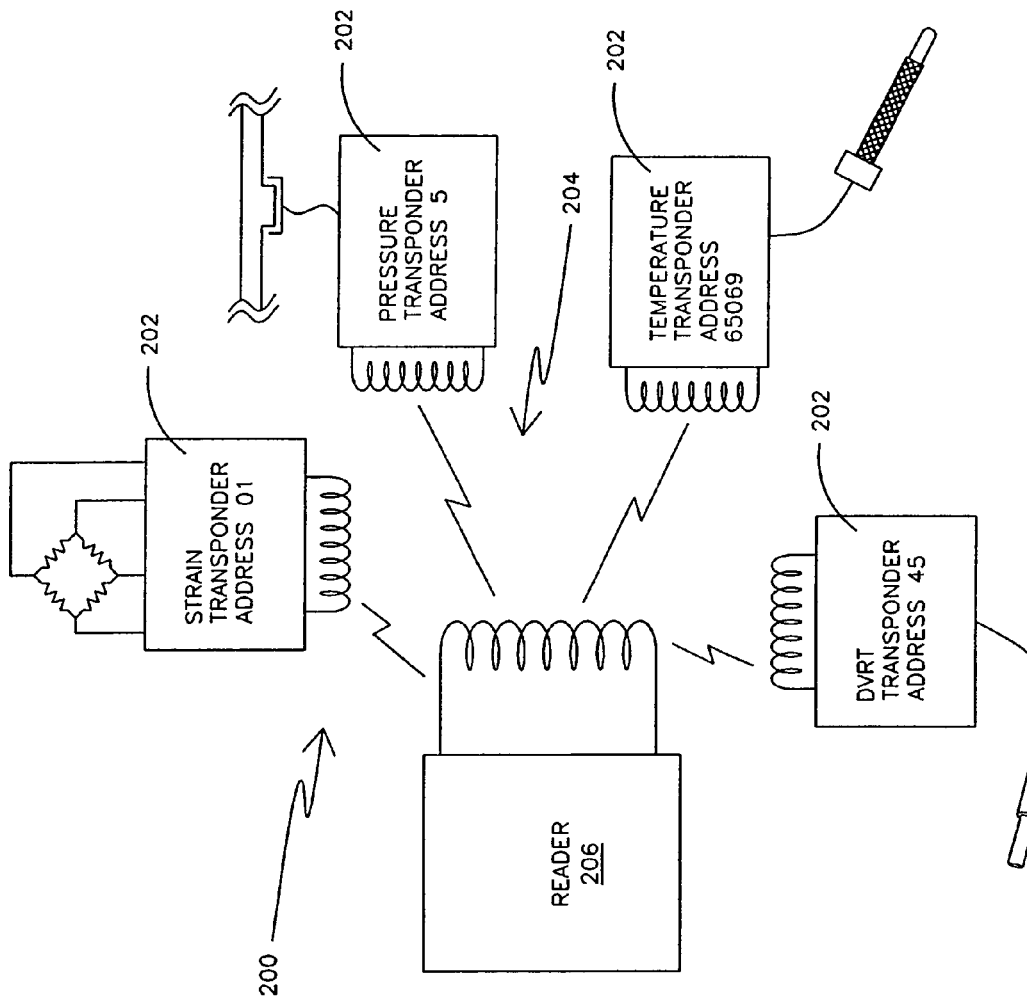
FIG. 8a is a schematic block diagram of multiple addressable transponders all being powered by the same reader and all communicating their data via switched reactance in a randomly time delayed fashion to avoid collisions.
Figure 8B:
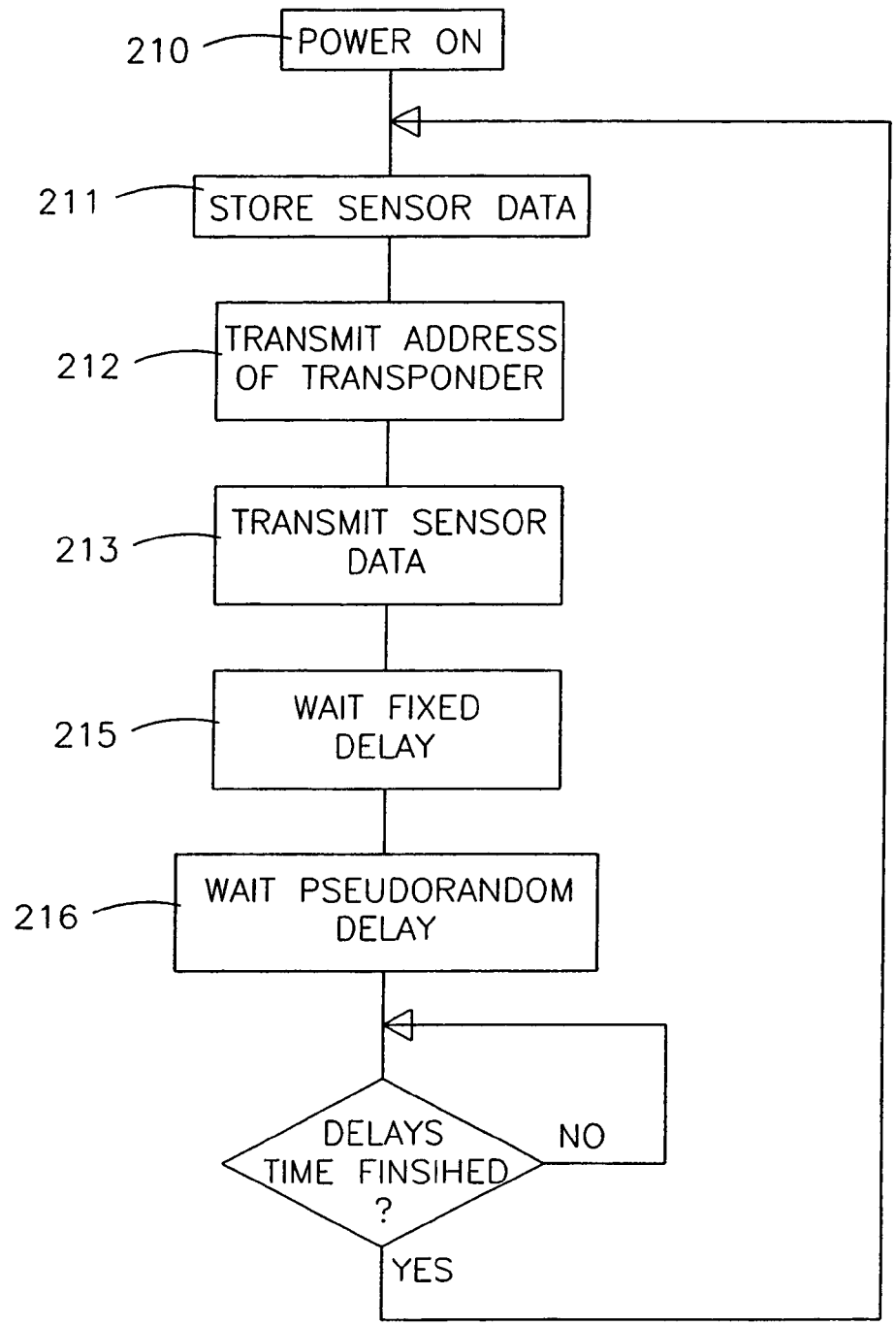
FIG. 8b is a flow chart showing firmware for encoding in a microcontroller for controlling transmission timing from each sensor transponder of a network of sensor transponders.

Programmable microcontroller 54 as controlling element in transponder 48 allows a great deal of flexibility in sensing system 200 to be realized for the first time, as shown in FIG. 8a. For example, firmware can now be designed, as shown in the flowchart of FIG. 8b, to support networking communications formats that allow multiple sensor transponders 202 within a single excitation field 204 to be interrogated by single reader 206, as shown in FIG. 8a and the flowchart in FIG. 8b. Each sensor transponder 202 has a unique address, and each sensor transponder 202 communicates its unique address along with the sensor data. Because of the address, reader 206 can thereby distinguish sensor data from hundreds of sensor transponders 202 that may be communicating with reader 206. The firmware program illustrated in the flow chart of FIG. 8b is preferably included in a hard wired device such as EEPROM 208 included in microprocessor 54 (FIG. 2a) or a flash programmable device that may be included in microprocessor 54 or with microprocessor 54.

A protocol in which sensor data is randomly periodically transmitted from each addressable sensor transponder 202 can accommodate hundreds of sensor transponders 202 in a single excitation field 204. Sensor transponders 202 may be randomly distributed in concrete, for example, to provide information during curing, or to provide information about the deterioration of the concrete over an extended time, such as crack formation or corrosion of reinforcing bars in the concrete. Collisions between sensor transponder communications may be avoided, as shown in the program illustrated in FIG. 8a, by providing a fixed time delay plus a randomization time delay in the communication from each sensor transponder 202.

Microprocessor 54, included in each sensor transponder 202 (see FIGS. 2a, 8a, 8b) instructs each transponder 202 to modulate its receiver coil to transmit sensor address and sensor data after the fixed time interval plus the random time interval has passed. To minimize the probability of a collision the fixed delay time is increased as more sensor transponders 202 are provided within radiation field 204. This fixed delay time number can be factory provided given the number of sensor transponders ordered or it can be reset in the field if bidirectional communication is included, as shown in FIGS. 2a–2c.

Since each sensor transponder 202 can have onboard memory or data storage 208, and since they can all be remotely powered simultaneously by reader 206, it is possible for all sensor transponders 202 to acquire and store sensor data simultaneously even though they transmit the data at different times. Additional or alternate non-volatile data storage can also be provided, such as static RAM, magnetic RAM, or flash memory. They can then communicate the stored data back to reader 206 later randomly and one at a time. Furthermore, by logging the data in data storage 208, energy is saved compared to immediate serial transmission, allowing increased distance between transponder and reader while acquiring data, especially in the embodiment using RF transmission, shown in FIG. 2b. If a static RAM storage device is used then battery or capacitor backup power is preferably available to retain data.

As shown in FIG. 8b, once reader 206 is provided nearby sensor transponders 202, sensor transponders 202 receive power transmitted from reader 206 and power turns on for them, as shown in box 210. Sensor 60, 60' can now start acquiring data and storing sensor data in EEPROM data storage 208, as shown in box 211. Microprocessor 54 now directs transmission of its sensor transponder's address and the acquired sensor data, as shown in boxes 212 and 213. Microprocessor 54 then provides a fixed time delay by executing a software loop at a rate determined by clock cycles of its internal RC clock circuit 214. It executes this loop a number of times determined by a stored number that sets the fixed delay, thus providing the programmed magnitude of the fixed time delay (FIG. 2a–2c), as shown in box 215. Microprocessor 54 also provides a random time delay using a random number generator software routine to generate a random number to apply to the same software loop, as shown in box 216 of FIG. 8b, to provide the random time delay. At each step in the software loop microprocessor 54 decides whether the fixed or random number has been reached, If not, microprocessor 54 continues to cause delay. If the number has been reached, microprocessor 54 causes repetition of the entire process starting with sensor 60,60' providing another measurement and storing its sensor data, as shown in box 211.

Figure 8C:
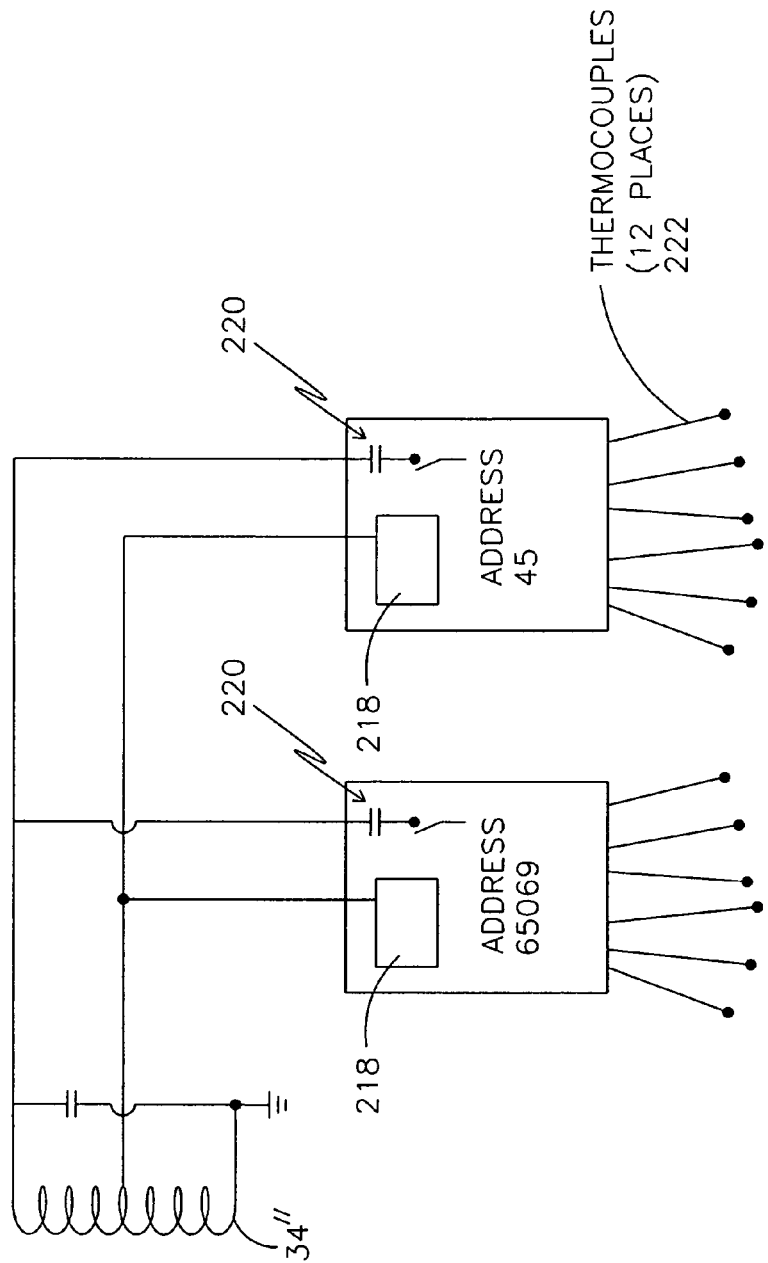
FIG. 8c is a schematic block diagram of multiple addressable transponders all being powered by the same reader and all also being powered from the same receiver coil.

In another embodiment multiple sensor transponder circuits 218 can be provided with a single receiver coil 34' and receiver tank circuit 28, as shown in FIG. 8c. Switched reactance circuit 220 is connected to each addressable sensor transponder circuit 218. Each addressable sensor transponder circuit 218 includes microprocessor 54, power supply elements 50 and 52, sensors 60, 60' and other elements shown in FIGS. 2a, 2c. Switched reactance circuit 220 in each addressable sensor transponder circuit 218 transmits both address and sensor data. MUX 56 in microprocessor 54 sequentially provides data to data storage in microprocessor 56 from individual sensors 60,60', such as thermocouples 222. From the sequence of data arrival, the specific thermocouple 222 providing the data can be determined. Software in an external computer can be used to provide this level of sensor identification based on sequence of arrival. Providing multiple sensor circuits 218 with a single receiver coil saves space, allowing many sensors to be in a single small package. Alternatively, RF transmitters can be provided with each sensor transponder 218 as shown in FIG. 2b. Two way communication can also be provided with ASK or FSK demodulators, as shown in FIGS. 8a–8c.

Energy Storage

A further advantage of the periodic transmission from multiple addressable sensor transponders 202 described herein above is the ability of each transponder 202 to collect and store energy for reading sensors that may consume higher power to operate, such as low resistance strain gauges. Transponder 48c, having energy storage capacitor 220, shown in FIG. 2c, can be used in this embodiment. Microcontroller 54 monitors the voltage across capacitor 220 and powers excitation of sensors 60 for brief periods of time, only when enough power has been stored in capacitor 220. During the time between its periodic transmissions transponder 48c sleeps, gathering energy from reader 40 and storing this energy in capacitor 220 until sufficient energy has been stored and until microprocessor 54 indicates that the time has arrived to take a measurement using sensor 60 and to transmit the resultant data to reader 40. Energy storage capacitor 220 in FIG. 2c can be replaced with another energy storage device, such as a rechargeable battery. The stored energy can also be used to log data from sensors 60 for later transmission to reader 40. Stored energy capacitor 220 and data storage device 208 allows reader 40 to be only sporadically available while allowing sensor measurements to be made much more often, reducing energy consumption and increasing energy efficiency.

Ratiometric Sensor Detection

As shown in FIG. 2a the excitation signal picked up by tap 66 on receiver coil 34' can be used to drive sensor transponder circuitry 48a as well as sensor 60 itself. This is particularly attractive for sensors that require AC excitation but is not limited to such sensors. The advantage is that need for an oscillator on the sensor transponder is eliminated, as described in commonly assigned U.S. Pat. No. 6,622,567, which describes borrowing power from a receiver coil to power an AC excited sensor, such as a DVRT.

One disadvantage of using energy from receiver coil 34 to provide an AC signal to an AC sensor, such as a DVRT, is that a change in distance between reader coil 40 and receiver coil 34 modulates the intensity of that AC signal received at the AC sensor 60', as shown in FIG. 3. The present inventors recognized a way to get around that drawback by making the output of sensor 60' provided at A-B in FIG. 3 ratiometric with the magnitude of the AC signal delivered to sensor 60' at tap 66. The benefit of providing a ratiometric output is that as distance between receiver coil 34' and reader coil 38 changes the output of sensor 60' remains substantially unchanged.

The sum of voltages at points A and B is equal to the magnitude of the AC signal at tap 66. The difference in potential between A and B is the output of sensor 60'. The ratio of the difference to the sum is the desired ratiometric signal. Because the difference signal depends on the sum signal the ratio of the two is independent of the sum signal and independent of the distance to reader 40.

Alternatively, the ratio of rectified signals can be used. In this case, the ratio of Ar-Br to Vp is used, where Vp is the rectified signal from tap 66. Outputs A and B can be rectified using rectifiers 230 becoming rectified outputs $A_R$ and $B_R$ respectively, as shown in FIG. 3. These rectified sensor output signals can be amplified with a difference amplifier, such as amplifier 58 shown in FIGS. 2a–2c and digitized in A/D converter 230. In addition, signal rectified input signal 67, Vp from tap 66 can be measured by microcontroller 54, as also shown in FIGS. 2a–2c. Microcontroller 54 does the math to provide $(A_R-B_R)/V_p$, which is rectified sensor output $A_R-B_R$ ratiometric with the magnitude of the excitation voltage $V_p$ available from receiver coil 34'.

Reader Optimization

Data coming back to reader 40 from sensor transponder 48a, 48c (FIGS. 2a, 2c) can be read by circuits in reader 250, as shown in FIG. 9a. In sensor transponder systems 48a, 48c using switched reactance, data received by reader coil 38 of reader 250 is represented by variations in voltage 252 across reader coil 38, as shown in FIG. 9b. These variations in voltage 252 across reader coil 38 are caused by switched reactance circuit 30 connected to sensor transponder 48a, 48c (FIGS. 2a, 2c).

Many methods can be used to convert this varying electromagnetic signal into meaningful data, including such a well known method as AM envelope demodulation that is widely used in ordinary radios and for reading ordinary RFID tags that do not have sensor transponders. Existing off-the-shelf RFID systems typically use envelope demodulation in which the excitation signal is simply rectified and low pass filtered to remove the carrier wave from oscillator 253 while passing the changes in amplitude of the carrier wave that are provided by switched reactance in sensor transponder 48a, 48c occurring at a designated data rate.

In addition, the present inventors found that synchronous AM demodulation, commonly used in broadcast or military grade AM radio receivers and as a signal conditioner for DVRTs provides improved signal to noise ratio. Synchronous AM demodulation has not heretofore been used for reading RFID tags. The present inventors also developed a new scheme for converting the signal received at coil 38 to meaningful data, which they called impedance bridge demodulation, more fully described herein below. They also found that phase demodulation, widely used as one method of detecting RF data communications radios, can be used.

Envelope demodulation type reader 250 is illustrated in FIG. 9a. A typical signal to be demodulated from excitation reader coil 38 consists of very high amplitude carrier 252 originating in oscillator 253 with as little as 1% amplitude modulation (AM) of the data caused by sensor transponder 48a, 48c, as shown in FIGS. 2a, 2c and FIG. 9b.

Oscillator 253 provides AC power to reader coil 38 which generates an electromagnetic signal that is received by receiver coil 34' and modified by switched reactance transponder 48a, 48c. But this AC power from oscillator 253 includes harmonic distortion products and phase noise. In addition, this AC power from oscillator 253 is loaded down by changes introduced by sensor transponder 48a, 48c as its switched reactance switches. The desired signal are the changes introduced by this loading, and envelope demodulation allows detecting the loading signal on the carrier wave despite the presence of the distortion products and the phase noise. Using envelope demodulation, the sum of carrier 252, distortion products, phase noise and modulation induced by sensor transponder 48a, 48c (FIGS. 2a, 2c), are rectified in diode D1, low pass filtered in low pass filter 254, and amplified and level shifted to TTL or RS 232 levels in comparator amplifier CMP 256, providing recovered data stream 258 shown in FIG. 9d. Data stream 258 has the high frequency carrier component removed and only includes the envelope of that carrier as modified by loading from sensor transponder 48a, 48c. While this is a reasonably effective method, it works as long as the loading from sensor transponder 48a, 48c is greater in magnitude than distortion and phase noise from carrier oscillator 253. Thus, this method works best when oscillator 253 has high spectral purity and provides high amplitude stability for the carrier.

The present inventors found that one improvement is to use synchronous demodulation reader 260, as shown in FIG. 10a to obtain recovered data similar to that shown in FIG. 9d but with higher signal to noise ratio, allowing reader 40 to be further away from sensor transponder 48a, 48c. In this method, synchronous demodulator 261 replaces diode D1. Synchronous demodulator 261 is an active device that facilitates removal of distortion products and phase noise before the signal is filtered and amplified, thus improving signal to noise ratio. Synchronous demodulator 261 includes gain polarity switch 262 and operational amplifier 263. Gain polarity switch 262 is an electronic switch controlled by the carrier from oscillator 253, including its signal, distortion products and phase noise. The output from operational amplifier 263 is rectified at the sum of the input frequencies, or about twice the frequency of oscillator 253. The output from operational amplifier 263 also includes a DC shift that depends on the magnitude of the loading introduced by sensor transponder 48a, 48c. The result of the synchronous demodulation process is an output signal with less noise and distortion than would be obtained with the diode of FIG. 9a as shown in FIG. 10b.

This amplitude modulation signal is then low pass filtered in low pass filter 264, providing a signal similar to that shown in FIG. 9c except it can be at lower amplitude because of the higher signal to noise ratio. To allow transmission of this low amplitude signal it is first amplified by comparator amplifier and slicer 266, and then level shifted by level shifter 268 as required for connection to a standard RS 232 serial interface. In practice higher order distortion products and some noise still appear in this output, but a much higher signal to noise ratio can be achieved with this method when compared to envelope demodulation since many of the distortion and noise components present in the carrier are effectively cancelled prior to amplification.

Another method of detecting small load impedance changes in reader 270 having reader coil 38 is to use impedance bridge 271 between reader carrier oscillator 272 and reader coil 38, as shown in FIG. 11a. This impedance bridge configuration is balanced and at null for one state of the incoming data and unbalanced by changes in loading induced by switched reactance sensor transponder 48a, 48c and receiver coil 34 communicating data. When the load impedance of reader coil 38 is equal to the impedance of impedance bridge 271 the signal at differential amplifier 274 is zero. When sensor transponder 48a, 48c loads reader coil 38, its impedance is no longer equal to the impedance of impedance bridge 271, and the signal at differential amplifier 274 is no longer zero. The imbalance in the impedance bridge induced by this state of the data is amplified by difference amplifier 274. The resultant output is an AM signal with a percentage of modulation proportional to the level of balance or imbalance of impedance bridge 271.

Without impedance bridge 271, carrier 276 would have only about 1% amplitude modulation, as shown in FIG. 11b. With proper balance of impedance bridge 271, nearly 100% modulation can be achieved, as shown by carrier 278 in FIG. 11c. Difference amplifier 274 amplifies the part of the carrier wave that is modulated by receiver coil 34, shown FIG. 2a, which is the data from sensor transponder 48a. This signal is then envelope demodulated. Since impedance bridge 271 is a passive device, new distortion products are not introduced and the available signal to noise ratio is higher than envelope demodulation alone would provide.

Figure 12:
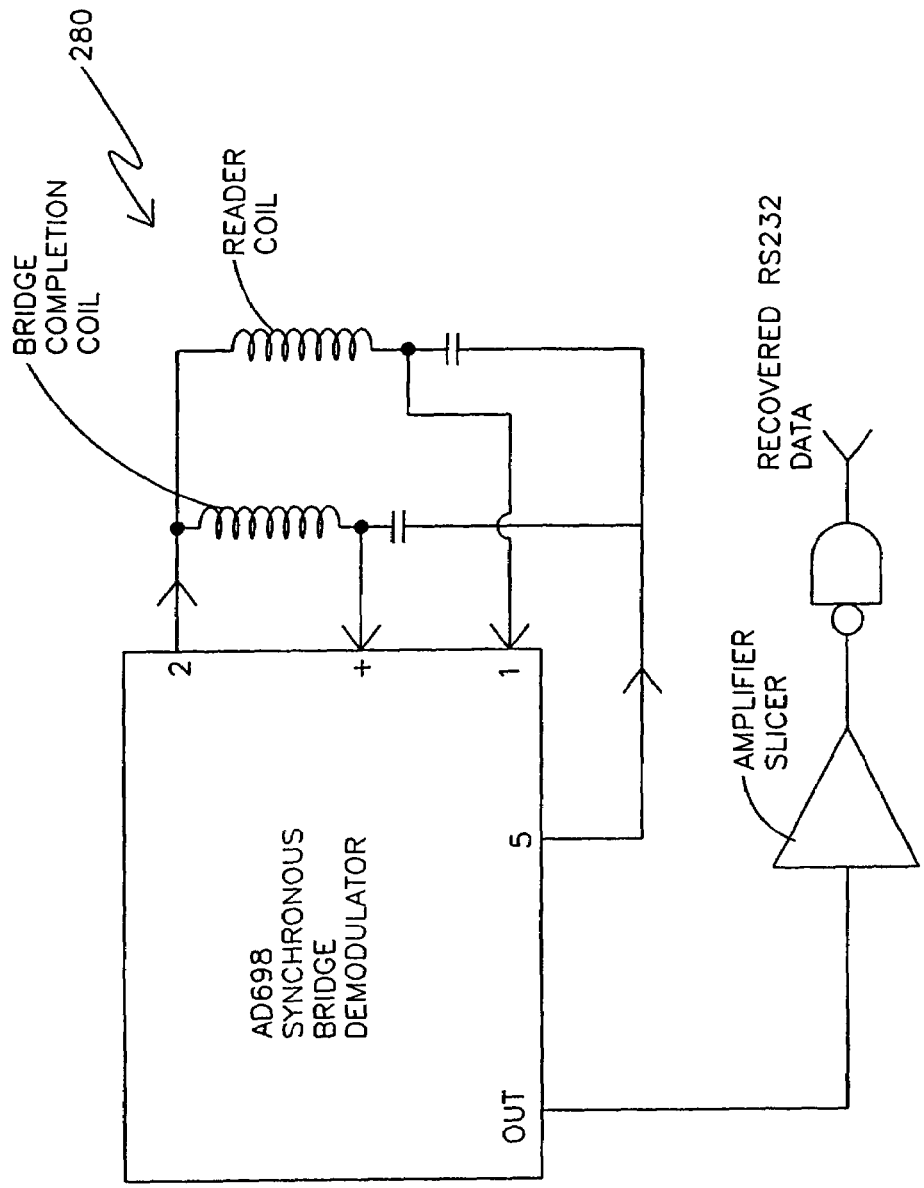
FIG. 12 is a schematic block diagram of another embodiment of a reader of the present invention providing synchronous AM demodulation using an AD698 synchronous bridge demodulator for demodulation of the carrier signal as modified by the switched reactance circuit of a sensor transponder of the present invention.

The present inventors also found improvement by providing reader 280 having a combination of impedance bridge and synchronous demodulation. The synchronous demodulation may be provided based on the AD698 (Analog Devices, Norwood Mass.) signal conditioner IC 282, as shown in FIG. 12. This IC is intended for signal conditioning in linear variable differential transformer (LVDT) and differential variable reluctance transducer (DVRT) sensors. However, the present inventors found a new use for the AD698 since it provides most of the necessary components for a reader, such as reader 40 shown in FIGS. 2a–2c, including a low noise, high output carrier oscillator with differential outputs, and synchronous demodulation. The inventors found that since the chip is optimized for use in full differential Wheatstone bridge circuit, it can be combined with impedance bridge demodulation coils 284 for use in combination with reader coil 286 to provide the impedance bridge. The AD698 circuit has advantage since a small number of components can be used, providing low cost, small size, and simple design for reader 280. Other IC's such as the Philips 5521 LVDT signal conditioner also contain components that can be used to build an integrated reader for combining synchronous demodulation and impedance bridge demodulation.

Figure 13:
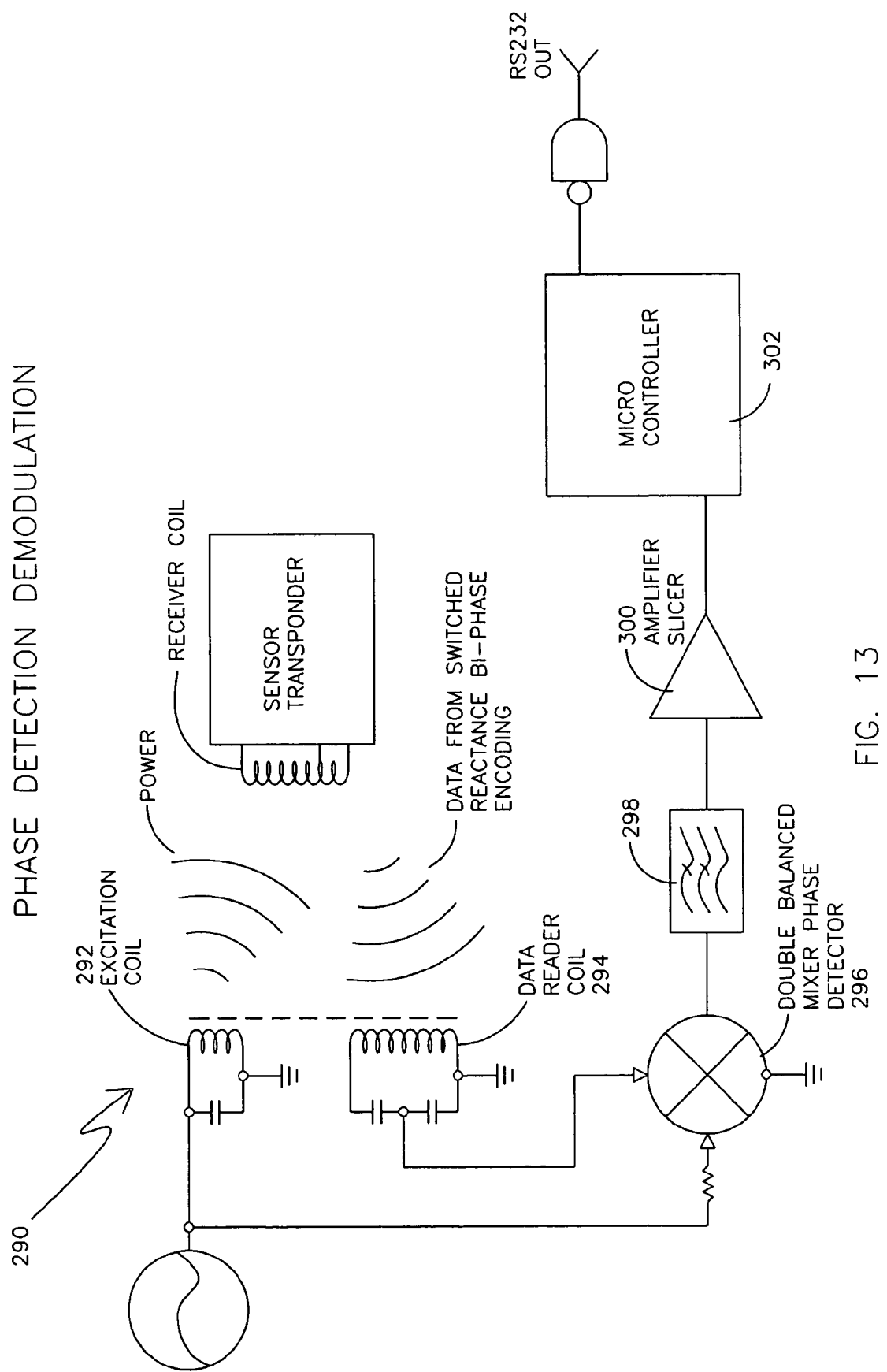
FIG. 13 is a schematic block diagram of another embodiment of a reader of the present invention providing phase detection demodulation of the carrier signal as modified by the switched reactance circuit of a sensor transponder of the present invention.

Still another embodiment of a high performance reader employs phase detection reader 290, as shown in FIG. 13. Rather than a single reader coil this embodiment uses two separate coils, excitation coil 292 for transmitting power to sensor transponder 34 and data reader coil 294 for reading data from transponder 34. Double balanced mixer 296 acts as a phase detector to output a varying DC signal that is proportional to the phase angle between signals on excitation coil 292 and on data reader coil 294. The data stream from sensor transponder 48a, 48c modulates the signal received by data reader coil 294 and this modulation is detected as a shift of the phase angle at the output of double balanced mixer 296.

This technique produces the highest signal to noise ratio of the embodiments described here because the phase detection scheme completely removes the carrier signal. This is because the carrier frequency component appears at both inputs to the double balanced mixer and the phase angle is provided as an output along with twice the frequency of the carrier signal. The high frequency signal is removed in low pass filter 254, leaving only the phase angle information. This phase angle is amplified in amplifier slicer 256 and sent to RS232 output 258 as before. Alternatively the amplified phase angle data can be provided to microcontroller 94, as described in FIG. 7 when the data from sensor transponder 48a, 48c is Manchester or biphase encoded, as described herein above.

Calibration of Sensor Transponder Electronics

Signal conditioning electronic components can drift over time or with temperature. These changes in signal conditioning electronics can affect the accuracy of readings from sensor transponder 48a–48c, and therefore the signal conditioning electronics in sensor transponder 48a–48c should be calibrated from time to time. Furthermore the conversion of voltage readings from sensors to physical units, such as strain or pressure, should be calibrated and this calibration should also be performed from time to time. These calibrations may be difficult for sensors that have been hermetically packaged, implanted, potted, positioned on a spinning turbine, or otherwise positioned with difficult access.

The present inventors provide shunt calibration, as shown in FIGS. 2a–2c, in which known resistance or known reactance 310 is switchably connected across a sensor, such as one of the legs of sensor bridge circuit 312, as shown in FIGS. 2a–2e. Sensors, such as a strain sensor, torque transducer, thermistor DVRT, variable capacitor device, or any other sensor can be calibrated in this manner. The shunt reactance can be a known capacitance or a known inductance. If the sensor is a DC sensor, than a shunt resistance is used. If the sensor is an AC sensor, than a shunt reactance is used.

The shunt calibration can be performed on demand for sensor transponders, such as sensor transponders 48a–48c, under the control of microcontroller 54. No bidirectional communication is needed in this scheme. It can be performed automatically, for example, such as on startup of sensor transponder 48a–48c under the control of microprocessor 54. In this case bidirectional communication is not needed. The calibration information can be sent to reader 40 so reader 40 can provide the coefficients to the sensor data it receives, as required to adjust the data it receives. Alternatively the calibration information can be applied locally by microcontroller 54 within sensor transponder 48a–48c to provide correction before communication to reader 40.

Bidirectional Communication

Amplitude Shift Keyed (ASK) demodulator 320 can be included to provide for receiving information from the reader, as also shown in FIG. 2a. ASK demodulator 320 senses a shift in the amplitude of signal received by coil 34' because of modulation of carrier signal from oscillator 251 in reader 40, providing a digital input to microprocessor 54 in sensor transponder 48a–48c. In this case Vp line 67, which is rectified power received before voltage regulation, is used for digital communications into sensor transponder 48a, 48b, 48c. Alternatively, a Frequency Shift Key (FSK) demodulator, as described in commonly assigned U.S. Pat. No. 6,529,127, incorporated herein by reference, can be used, replacing ASK demodulator 320. In yet another alternative RF transmitter 96 in FIG. 2b can be an RF transceiver which receives and transmits radio frequency data.

Bidirectional communication allows reprogramming microcontroller 54. It can also be used to trigger the start of data logging from sensor transponders, initiate transmission of stored data, or initiate a calibration. Although the system is powered only when a reader is nearby, the initiation of these functions with bidirectional communication allows selecting which of a large number of sensor transponders performs any of these functions. Thus communication from networked sensor transponders is enabled while avoiding communication collisions.

The present inventors found that with the techniques described herein, sensor data can be communicated from exceedingly harsh environments, such as where batteries may need to be eliminated, crystals are likely to fail, physical space is limited, or wired connections are undesirable. Such a system has application in medical, aerospace, industrial, and civil infrastructure environments.

While several embodiments of the invention, together with modifications thereof, have been described in detail herein and illustrated in the accompanying drawings, it will be evident that various further modifications are possible without departing from the scope of the invention. Nothing in the above specification is intended to limit the invention more narrowly than the appended claims. The examples given are intended only to be illustrative rather than exclusive.

What is claimed is:

1. An electronic system, comprising a reader and a remotely powered and remotely interrogated sensor transponder, said sensor transponder including:

a housing containing said sensor transponder, wherein said housing is hermetically sealed;

a radiation receiving device connected for receiving power, wherein all power for operating said sensor transponder is derived from power radiated from said reader and received by said radiation receiving device;

a processor connected to receive power derived from said radiation receiving device;

a sensor connected to provide sensor data to said processor;

a transmitting device connected to receive power derived from said radiation receiving device and connected for transmitting data derived from said sensor to said reader, wherein no feed through from said transmitting device passes through said housing;

a data receiving device, wherein said data receiving device is connected for receiving digital data derived from said reader and for providing said digital data to said processor.

2. An electronic system as recited in claim 1, wherein said sensor comprises an analog device.

3. An electronic system as recited in claim 2, wherein said sensor transponder further comprises an analog/digital converter.

4. An electronic system as recited in claim 1, wherein said transmitting device includes a switched reactance circuit.

5. An electronic system as recited in claim 4, wherein said switched reactance circuit comprising a reactive component connected to switchably affect electromagnetic radiation radiated from said reader.

6. An electronic system as recited in claim 5, wherein said reader includes a radiation transmitting device, wherein said reader comprises a circuit to detect changes in loading of said radiation transmitting device, as a result of switching of said switched reactance circuit in said sensor transponder.

7. An electronic system as recited in claim 1, wherein said radiation receiving device comprises at least one from the group including a tap and a capacitive divider for providing power to at least one from the group including said sensor and said processor.

8. An electronic system as recited in claim 7, wherein said radiation receiving device comprises multiple taps, wherein tap location is dynamically selected depending on loading to provide impedance matching and efficient energy transfer.

9. An electronic system as recited in claim 1, wherein said housing comprises a metal enclosure and wherein said radiation receiving device is tuned to receive radiation at a frequency sufficiently low so a substantial portion of said radiation is able to penetrate through said metal enclosure.

10. An electronic system as recited in claim 9, wherein said frequency is less than 125 kHz.

11. An electronic system as recited in claim 9, wherein said frequency is less than about 44 kHz.

12. An electronic system as recited in claim 9, wherein said frequency of about 4 kHz.

13. An electronic system as recited in claim 1, wherein said sensor transponder is for implanting in living tissue.

14. An electronic system as recited in claim 13, wherein said sensor transponder is for implanting in a bone.

15. An electronic system as recited in claim 1, wherein said processor includes an integrated clock.

16. An electronic device as recited in claim 15, wherein said integrated clock comprises an RC clock.

17. An electronic system as recited in claim 1, wherein said sensor transponder further includes a non-volatile memory for storing sensor data.

18. An electronic system as recited in claim 1, wherein said sensor transponder further includes an energy storage device.

19. An electronic system as recited in claim 1, wherein said energy storage device is connected to provide a higher power to said sensor than is available from said radiation receiving device.

20. An electronic device as recited in claim 1, further comprising a receiver resonant tank circuit and a power-using device, said receiver resonant tank circuit for receiving electromagnetic radiation for powering said power-using device, said receiver resonant tank circuit including said radiation receiving device, wherein said radiation receiving device includes a first end and a second end, wherein said receiver resonant tank circuit further includes an impedance matching circuit, wherein said impedance matching circuit is connected to said radiation receiving device to provide greater current to said power-using device than would be available to said power-using device if said power-using device were connected between said first and said second end.

21. An electronic device as recited in claim 20, wherein said impedance matching circuit comprises a tap between said first and said second end.

22. An electronic device as recited in claim 21, wherein said tap is provided at a location between said first end and said second end so said power-using device does not substantially degrade Q factor of said receiver resonant tank circuit.

23. An electronic device as recited in claim 20, wherein said impedance matching circuit comprises a plurality of taps between said first and said second end, wherein connection is switchably provided to one of said plurality of taps to most closely impedance match to impedance of said power using device.

24. An electronic device as recited in claim 20, wherein said impedance matching circuit comprises a capacitive divider.

25. An electronic device as recited in claim 24, wherein said capacitive divider provides an output set so said power-using device does not substantially degrade Q factor of said receiver resonant tank circuit.

26. An electronic device as recited in claim 20, wherein said impedance matching circuit provides an output so impedance of said power-using device approximately matches impedance presented by said radiation receiving device at said output.

27. An electronic device as recited in claim 20, wherein said impedance matching circuit provides an output so power transfer to said receiver resonant tank circuit from said electromagnetic radiation is not substantially degraded for expected power consumption of said power-using device.

28. An electronic device as recited in claim 20, wherein said impedance matching circuit provides an output so power transfer to said power-using device from said receiver resonant tank circuit is optimized for expected power consumption of said power-using device.

29. An electronic device as recited in claim 20, wherein said impedance matching circuit has an output that can be dynamically varied during operation under the control of said processor, so power transfer to said receiver resonant tank circuit from said electromagnetic radiation is optimized for power actually being consumed by said power-using device and so power transfer to said power-using device from said receiver resonant tank circuit is optimized for expected power consumption of said power-using device.

30. An electronic device as recited in claim 1, wherein said reader includes an rf receiver, wherein said transponder includes an rf transmitter for transmitting data to said reader.

31. An electronic system as recited in claim 1, further comprising a plurality of said remotely powered and remotely interrogated sensor transponders, wherein each said sensor transponder is connected for receiving all power for operating said sensor transponder derived from power radiated from said reader, wherein each said sensor transponder has an address and wherein each said sensor transponder has a system to transmit data so as to avoid collisions.

32. An electronic system as recited in claim 31, wherein said system to avoid collisions includes a random timing generator.

33. An electronic system as recited in claim 31, wherein each of said plurality of sensor transponders includes data logging.

34. An electronic system as recited in claim 31, wherein each of said plurality of networked sensor transponders includes energy storage.

35. An electronic system as recited in claim 31, wherein each of said plurality of networked sensor transponders includes two way communication.

36. An electronic system as recited in claim 1, wherein said transponder is part of a medical implant.

37. An electronic system as recited in claim 1, wherein said transponder is part of an orthopedic implant.

38. An electronic system as recited in claim 1, further comprising an orthopedic implant facing said transponder, wherein said transponder senses position with respect to said orthopedic implant.

39. An electronic system as recited in claim 38, wherein said transponder includes a sensor for measuring distance between said sensor and said orthopedic implant.

40. An electronic system as recited in claim 39, further comprising a component between said sensor and said orthopedic implant, wherein a change in said distance between said sensor and said orthopedic implant is a measure of wear of said component.

41. An electronic system as recited in claim 1, wherein said sensor comprises at least one from the group including a displacement sensor, a pressure sensor, a force sensor, a torque sensor, and a temperature sensor.

42. An electronic system as recited in claim 41, wherein said displacement sensor comprises a variable reluctance transducer.

43. An electronic system as recited in claim 1, further comprising a member subject to corrosion, wherein said sensor is located to detect corrosion of said member.

44. An electronic system as recited in claim 43, wherein said transponder can transmit at least one from the group including a change in said sensor data and sensor data within an acceptable limit.

45. An electronic system as recited in claim 1, wherein said transmitting device includes a switched reactance circuit.

46. An electronic system as recited in claim 1, wherein said a radiation receiving device includes at least one from the group including a coil and an antenna.

47. An electronic system as recited in claim 1, wherein said data receiving device includes a demodulator.

48. An electronic system as recited in claim 1, further comprising an RE transceiver, wherein said data receiving device and said transmitting device are included in said RE transceiver.

49. An electronic system as recited in claim 1, wherein said processor is connected to receive said digital data for performing at least one from the group including: reprogramming said processor, triggering data logging, initiating transmission of stored data, and initiating calibration.

50. An electronic system, comprising a reader and a remotely powered and remotely interrogated sensor transponder, said sensor transponder including:
a radiation receiving device connected for receiving power, wherein all power for operating said sensor transponder is derived from power radiated from said reader and received by said radiation receiving device;
a processor connected to receive power derived from said radiation receiving device;
a sensor connected to provide sensor data to said processor;

a circuit connected to said sensor for performing sensor calibration; and a transmitting device connected to receive power derived from said radiation receiving device and connected for transmitting data derived from said sensor to said reader.

51. An electronic system as recited in claim 50, wherein said circuit for performing sensor calibration includes at least one from the group including a known resistance and a known reactance switchably connected across said sensor.

52. An electronic system as recited in claim 50, wherein said circuit for performing sensor calibration is under processor control.

53. An electronic system as recited in claim 50, wherein said processor includes a program to perform said sensor calibration automatically.

54. An electronic system as recited in claim 50, wherein at least one from the group including said processor and said reader includes a program to adjust sensor data based on results of said calibration.

55. An electronic system as recited in claim 50, wherein said transmitting device includes a switched reactance circuit.

56. An electronic system as recited in claim 50, wherein said a radiation receiving device includes at least one from the group including a coil and an antenna.

57. An electronic system as recited in claim 50, further comprising a data receiving device, wherein said data receiving device includes at least one from the group including a demodulator and an RF transceiver, wherein said RF transceiver includes said data receiving device and said transmitting device.

58. An electronic system, comprising a reader and a remotely powered and remotely interrogated sensor transponder, said sensor transponder including:

a radiation receiving device connected for receiving power, wherein all power for operating said sensor transponder is derived from power radiated from said reader and received by said radiation receiving device;

a processor connected to receive power derived from said radiation receiving device;

a sensor connected to provide sensor data to said processor;

an RC clock connected to encode clock data with data derived from said sensor; and a transmitting device connected to receive power derived from said radiation receiving device and connected for transmitting clock data encoded with data derived from said sensor to said reader.

59. An electronic system as recited in claim 58, wherein said reader includes a processor programmed to recover sensor data from a signal including both sensor data and clock data.

60. An electronic system as recited in claim 58, wherein said sensor transponder can withstand forces higher than 90,000 G's.

61. An electronic system as recited in claim 58, wherein said transmitting device includes a switched reactance circuit.

62. An electronic system as recited in claim 58, wherein said a radiation receiving device includes at least one from the group including a coil and an antenna.

63. An electronic system as recited in claim 58, wherein said receiving device includes a demodulator.

64. An electronic system as recited in claim 58, further comprising an RF transceiver, wherein said receiving device and said transmitting device are included in said RF transceiver.

65. An electronic system, comprising a reader and a remotely powered and remotely interrogated sensor transponder, said sensor transponder including:

a radiation receiving device connected for receiving power, wherein all power for operating said sensor transponder is derived from power radiated from said reader and received by said radiation receiving device;

a processor connected to receive power derived from said radiation receiving device;

a sensor connected to provide sensor data to said processor;

an RE transmitter connected to receive power derived from said radiation receiving device and connected for transmitting data derived from said sensor; and a data receiving device, wherein said data receiving device is connected for receiving digital data derived from said reader and for providing said digital data to said processor.

66. An electronic system as recited in claim 65, further comprising an RE transceiver, wherein said data receiving device and said RE transmitter are included in said RF transceiver.

67. An electronic system as recited in claim 65, wherein said actuator includes at least one from the group consisting of a solenoid, a pump, a motor, a mechanical switch, and a piezoelectric device.

68. An electronic system, comprising a reader and a remotely powered and remotely interrogated sensor transponder, said sensor transponder including:

a radiation receiving device connected for receiving power, wherein all power for operating said sensor transponder is derived from power radiated from said reader and received by said radiation receiving device;

a processor connected to receive power derived from said radiation receiving device;

a sensor connected to provide sensor data to said processor;

an actuator connected to receive power derived from said radiation receiving device;

a transmitting device connected to receive power derived from said radiation receiving device and connected for transmitting data derived from said sensor to said reader; and a data receiving device, wherein said data receiving device is connected for receiving digital data derived from said reader and for providing said digital data to said processor.

* * * * *